(12) United States Patent
Enokida et al.

(10) Patent No.: US 6,251,531 B1
(45) Date of Patent: *Jun. 26, 2001

(54) LIGHT-EMITTING MATERIAL FOR ORGANIC ELECTROLUMINESCENCE DEVICE, AND ORGANIC ELECTROLUMINESCENCE DEVICE FOR WHICH THE LIGHT-EMITTING MATERIAL IS ADAPTED

(75) Inventors: Toshio Enokida; Michiko Tamano; Satoshi Okutsu, all of Tokyo (JP)

(73) Assignee: Toyo Ink Manufacturing Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/030,791

(22) Filed: Feb. 26, 1998

Related U.S. Application Data

(62) Division of application No. 08/688,879, filed on Jul. 31, 1996, now Pat. No. 5,759,444.

(30) Foreign Application Priority Data

Feb. 25, 1995 (JP) .................................... 7-245607
Jan. 29, 1996 (JP) .................................... 8-12430

(51) Int. Cl.$^7$ .................................... H05B 33/14
(52) U.S. Cl. .................. 428/690; 428/704; 428/917; 313/504; 313/506
(58) Field of Search ................... 428/690, 704, 428/917; 313/504, 506

(56) References Cited

U.S. PATENT DOCUMENTS

| | | | |
|---|---|---|---|
| 5,061,569 | 10/1991 | VanSlyke et al. | 252/301.16 |
| 5,151,629 | * 9/1992 | Van Slyke | 313/504 |
| 5,456,988 | * 10/1995 | Sano et al. | 428/690 |
| 5,681,664 | * 10/1997 | Tamano et al. | 428/690 |

FOREIGN PATENT DOCUMENTS

| | | |
|---|---|---|
| 650955 | 5/1995 | (EP) . |
| 681019 | 11/1995 | (EP) . |
| 757088 | 2/1997 | (EP) . |

OTHER PUBLICATIONS

Toyo Ink Mfg Co. Ltd., Database WPI, Feb. 27, 1996, abstract, JP 8053397.

L.S. Sapochak & Al, "Luminescent Properties of Pentacoordinated Gallium Bis(2–Methyl–8–Hydroxyquinoline)(Carboxylate and Chloro) Compounds for OLED Applications" *Polymeric Material Science and Engineering,* vol. 72, pp. 331–332, 1995. (No month).

\* cited by examiner

*Primary Examiner*—Marie Yamnitzky
(74) *Attorney, Agent, or Firm*—Wenderoth, Lind & Ponack, L.L.P.

(57) ABSTRACT

A light-emitting material of the following general formula [1] for an organic electroluminescence device,

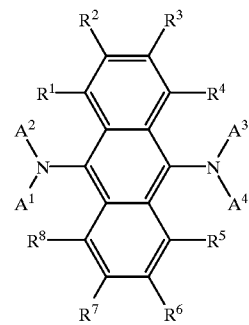

[1]

wherein each of $A^1$ to $A^4$ is a substituted or unsubstituted aryl group having 6 to 16 carbon atoms, and each of $R^1$ to $R^8$ is independently a hydrogen atom, a halogen atom, a substituted or unsubstituted alkyl group, a substituted or unsubstituted alkoxy group, a substituted or unsubstituted aryl group or a substituted or unsubstituted amino group, provided that adjacent substituents may form an aryl ring.

10 Claims, No Drawings

LIGHT-EMITTING MATERIAL FOR ORGANIC ELECTROLUMINESCENCE DEVICE, AND ORGANIC ELECTROLUMINESCENCE DEVICE FOR WHICH THE LIGHT-EMITTING MATERIAL IS ADAPTED

This application is a Divisional of Ser. No. 08/688,879 filed Jul. 31, 1996, U.S. Pat. No. 5,759,444.

BACKGROUND OF THE INVENTION

1. Field of the Invention

The present invention relates to a light-emitting material for an organic electroluminescence device (to be sometimes referred to as "EL device" hereinafter) used as a flat light source or a flat display device, and an EL device having a high brightness.

2. Description of the Related Art

An EL device using an organic substance is overwhelmingly expected to be usable as a solid light-emitting inexpensive large-screen, a full-color display device, and other devices are being developed in many ways. Generally, an EL device is composed of a light-emitting layer and a pair of mutually opposite electrodes sandwiching the light-emitting layer. Light emission is caused by the following phenomenon. When an electric field is applied to these two electrodes, the cathode injects electrons into the light-emitting layer and the anode injects holes into the light-emitting layer. When the electrons recombine with the holes in the light-emitting layer, their energy level shifts to a valence bond band which causes them to release energy as fluorescent light.

As compared with inorganic EL devices, conventional organic EL devices require high voltage, and their light emission brightness and light emission efficiency are low. Further, conventional organic EL devices deteriorate in properties to a great extent, and no organic EL device has been put to practical use.

There has been recently proposed an organic EL device which is produced by laminating a thin film containing an organic compound having a fluorescent quantum effect of emitting light at a low voltage (as low as less than 10 V) which has attracted attention (Appl. Phy. Lett., Vol. 51, page 913, 1987).

The above organic EL device has a light-emitting layer containing a metal chelate complex and a hole-injecting layer containing an amine-based compound, and emits green light having a high brightness. The above organic EL device achieves nearly practically usable performance, since it accomplishes a brightness of thousands $cd/m^2$ and a maximum light emission efficiency of 1.5 lm/W when a direct current voltage of 6 or 7 V is applied.

However, conventional organic EL devices including the above organic EL device are not yet sufficient in brightness thereby needing improvements in brightness to some extent. Further, their big problem is that they are unstable during continuous light emission operation over a long period of time. It is because, for example, the metal chelate complex such as tris(8-hydroxyquinolinate)aluminum complex is chemically unstable when light is emitted by the application of an electric field and because the metal chelate complex is poor in adhesion to a cathode so that the organic EL device deteriorates immensely in a short time during light-emitting operation. Therefore, in developing an organic EL device which has a higher light emission brightness and high light emission efficiency and which has excellent stability in continuous operation over a long period time, it is desirable to develop a light-emitting material having excellent light-emitting capability and durability.

SUMMARY OF THE INVENTION

It is an object of the present invention to provide an organic EL device which is excellent in light emission brightness and light emission effect and which has excellent stability in continuous operation over a long period of time.

According to the present invention, there is provided a light-emitting material of the following general formula [1] for an organic electroluminescence device,

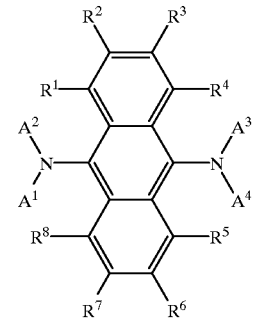

wherein each of $A^1$ to $A^4$ is a substituted or unsubstituted aryl group having 6 to 16 carbon atoms, and each of $R^1$ to $R^8$ is independently a hydrogen atom, a halogen atom, a substituted or unsubstituted alkyl group, a substituted or unsubstituted alkoxy group, a substituted or unsubstituted aryl group or a substituted or unsubstituted amino group, provided that adjacent substituents may form an aryl ring.

According to the present invention, further, there is provided a light-emitting material of the following general formula [2] for an organic electroluminescence device,

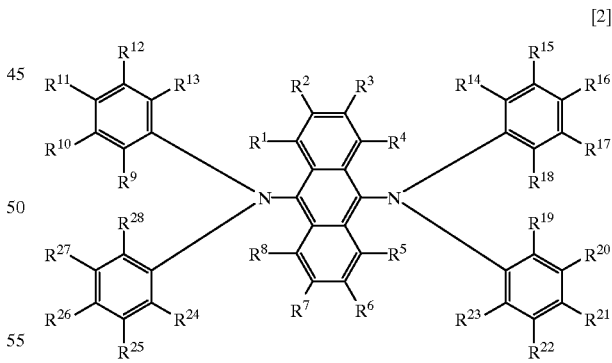

[2]

wherein each of $R^1$ to $R^{28}$ is independently a hydrogen atom, a halogen atom, a substituted or unsubstituted alkyl group, a substituted or unsubstituted alkoxy group, a substituted or unsubstituted aryl group or a substituted or unsubstituted amino group, provided that adjacent substituents of $R^1$ to $R^4$ or $R^5$ to $R^8$ may form an aryl ring.

According to the present invention, further, there is provided a light-emitting material of the following general formula [3] for an organic electroluminescence device,

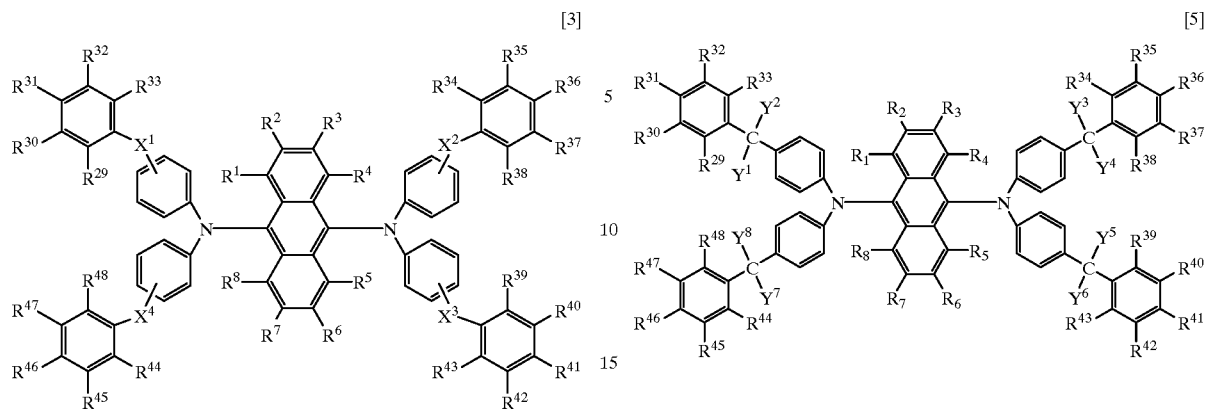

wherein each of $R^1$ to $R^8$ and $R^{29}$ to $R^{48}$ is independently a hydrogen atom, a halogen atom, a substituted or unsubstituted alkyl group, a substituted or unsubstituted alkoxy group, a substituted or unsubstituted aryl group or a substituted or unsubstituted amino group, and each of $X^1$ to $X^4$ is independently O, S, C=O, SO$_2$, $(CH_2)_x$—O—$(CH_2)_y$, a substituted or unsubstituted alkylene group or a substituted or unsubstituted alicyclic residue, provided that each of x and y is independently an integer of 0 to 20 and that x+y=0 in no case, provided that adjacent substituents of $R^1$ to $R^4$ or $R^5$ to $R^8$ may form an aryl ring.

According to the present invention, further, there is provided a light-emitting material of the following general formula [4] for an organic electroluminescence device,

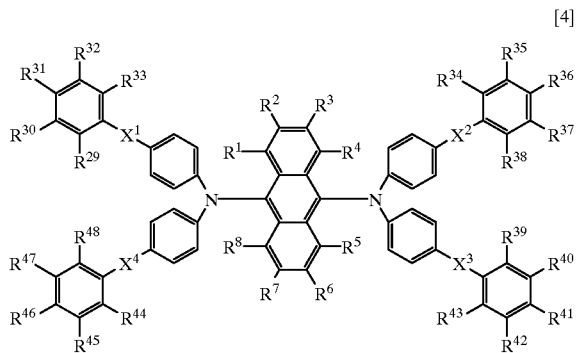

wherein each of $R^1$ to $R^8$ and $R^{29}$ to $R^{48}$ is independently a hydrogen atom, a halogen atom, a substituted or unsubstituted alkyl group, a substituted or unsubstituted alkoxy group, a substituted or unsubstituted aryl group or a substituted or unsubstituted amino group, and each of $X^1$ to $X^4$ is independently O, S, C=O, SO$_2$, $(CH_2)_x$—O—$(CH_2)_y$, a substituted or unsubstituted alkylene group or a substituted or unsubstituted alicyclic residue, provided that each of x and y is independently an integer of 0 to 20 and that x+y=0 in no case, provided that adjacent substituents of $R^1$ to $R^4$ or $R^5$ to $R^8$ may form an aryl ring.

According to the present invention, further, there is provided a light-emitting material of the following general formula [5] for an organic electroluminescence device, wherein each of $R^1$ to $R^8$ and $R^{29}$ to $R^{48}$ is independently a hydrogen atom, a halogen atom, a substituted or unsubstituted alkyl group, a substituted or unsubstituted alkoxy group, a substituted or unsubstituted aryl group or a substituted or unsubstituted amino group, and each of $Y^1$ to $Y^8$ is independently a substituted or unsubstituted alkyl group having 1 to 20 carbon atoms or a substituted or unsubstituted aryl group having 6 to 16 carbon atoms, provided that adjacent substituents of $R^1$ to $R^4$ or $R^5$ to $R^8$ may form an aryl ring.

Further, according to the present invention, there is provided an organic electroluminescence device obtained by forming a light-emitting layer or a plurality of thin organic compound layers including the light-emitting layer between a pair of electrodes which are an anode and a cathode, the light-emitting layer containing any one of the above light-emitting materials.

Further, according to the present invention, the above organic electroluminescence device has a layer containing an aromatic tertiary amine derivative or a phthalocyanine derivative, formed between the light-emitting layer and the anode.

Further, according to the present invention, the above aromatic tertiary amine derivative has the following general formula [6],

wherein each of $B^1$ to $B^4$ is independently a substituted or unsubstituted aryl group having 6 to 16 carbon atoms, and Z is a substituted or unsubstituted arylene group.

Further, according to the present invention, the above organic electroluminescence device has a layer containing a metal complex compound or a nitrogen-containing five-membered derivative, between the light-emitting layer and the cathode.

Further, according to the present invention, the above metal complex compound has the following general formula [7],

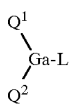

[7]

wherein each of $Q^1$ and $Q^2$ is independently a substituted or unsubstituted hydroxyquinoline derivative or a substituted or unsubstituted hydroxybenzoquinoline derivative, and L is a ligand which is halogen atom, a substituted or unsubstituted alkyl group, a substituted or unsubstituted cycloalkyl group, a substituted or unsubstituted aryl group which may contain a nitrogen atom, —OR in which R is a hydrogen atom, a substituted or unsubstituted alkyl group, a substituted or unsubstituted cycloalkyl group or a substituted or unsubstituted aryl group which may contain a nitrogen atom, or —O—Ga—$Q^3(Q^4)$ in which $Q^3$ and $Q^4$ have the same meanings as those of $Q^1$ and $Q^2$.

Further, according to the present invention, there is provided an organic electroluminescence device obtained by forming a plurality of thin organic compound layers including a light-emitting layer between a pair of electrodes, wherein the light-emitting layer contains any one of the above light-emitting materials, the device has an organic layer containing the compound of the general formula [6] between the light-emitting layer and the anode, and the device has an organic layer containing the compound of the general formula [7] between the light-emitting layer and the cathode.

DETAILED DESCRIPTION OF THE INVENTION

In the compound of the general formula [1], each of $A^1$ to $A^4$ is a substituted or unsubstituted aryl group having 6 to 16 carbon atoms. The substituted or unsubstituted aryl group having 6 to 16 carbon atoms includes phenyl, biphenyl, terphenyl, naphthyl, anthryl, phenanthryl, fluorenyl, pyrenyl, and these groups which may contain substituents which will be specifically described later. In each of the general formulae [1] to [5], carbon atom(s) of the aryl group may be replaced with at least one of a nitrogen atom, an oxygen atom and a sulfur atom. Further, in the formula [1], a combination of $A^1$ and $A^2$ may be an aryl group whose ring contains N in the general formula [1], or a combination of $A^3$ and $A^4$ may be an aryl group whose ring contains N in the general formula [1].

In the compounds of the general formulae [1] to [5], each of $R^1$ to $R^{48}$ is independently a hydrogen atom, a halogen atom, a substituted or unsubstituted alkyl group, a substituted or unsubstituted alkoxy group, a substituted or unsubstituted aryl group or a substituted or unsubstituted amino group. In each of $R^1$ to $R^{48}$, carbon atom(s) of the aryl group may be replaced with at least one of a nitrogen atom, an oxygen atom and a sulfur atom.

Specific examples of the substituents in $A^1$ to $A^4$ and specific examples of $R^1$ to $R^{48}$ are as follows. The halogen atom includes fluorine, chlorine, bromine and iodine. The substituted or unsubstituted alkyl group includes unsubstituted alkyl groups having 1 to 20 carbon atoms such as methyl, ethyl, propyl, butyl, sec-butyl, tert-butyl, pentyl, hexyl, heptyl, octyl and stearyl, and substituted alkyl groups having 1 to 20 carbon atoms such as 2-phenylisopropyl, trichloromethyl, trifluoromethyl, benzyl, α-phenoxybenzyl, α,α-dimethylbenzyl, α,α-methylphenylbenzyl, α,α-ditrifluoromethylbenzyl, triphenylmethyl and α-benzyloxybenzyl. The substituted or unsubstituted alkoxy group includes unsubstituted alkoxy groups having 1 to 20 carbon atoms such as methoxy, ethoxy, propoxy, n-butoxy, t-butoxy, n-octyloxy and t-octyloxy, and substituted alkoxy groups having 1 to 20 carbon atoms such as 1,1,1-tetrafluoroethoxy, phenoxy, benzyloxy and octylphenoxy. The substituted or unsubstituted aryl group includes substituted or unsubstituted aryl groups having 6 to 18 carbon atoms such as phenyl, 2-methylphenyl, 3-methylphenyl, 4-methylphenyl, 4-ethylphenyl, biphenyl, 4-methylbiphenyl, 4-ethylbiphenyl, 4-cyclohexylbiphenyl, terphenyl, 3,5-dichlorophenyl, naphthyl, 5-methylnaphthyl, anthryl, pyrenyl, and aryl groups whose carbon atom is replaced with a nitrogen atom, etc., such as furanyl, thiophenyl, pyrrolyl, pyranyl, thiopyranyl, pyridinyl, thiazolyl, imidazolyl, pyrimidinyl, triazinyl, indolyl, quinolyl, purinyl and carbazolyl. The substituted or unsubstituted amino group includes amino, dialkylamino groups such as dimethylamino and diethylamino, phenylmethylamino, diphenylamino, ditolylamino and dibenzylamino. Further, adjacent substituents ($A^1$ to $A^4$ and $R^1$ to $R^{48}$) may form phenyl, naphthyl, anthryl or pyrenyl.

In the compounds of the general formulae [3] and [4], each of $X^1$ to $X^4$ is independently O, S, C=O, $SO_2$, $(CH_2)_x$—O—$(CH_2)_y$, a substituted or unsubstituted alkylene group or a substituted or unsubstituted alicyclic residue, provided that each of x and y is independently an integer of 0 to 20 and that in no case x+y=0. Substituents of the substituted alkylene group or the substituted alicyclic residue are those which are specified as $R^1$ to $R^{48}$. The alkylene group of the substituted or unsubstituted alkylene group includes alkylene groups having 1 to 20 carbon atoms. The substituted alkylene group preferably includes 2-phenylisopropylene, dichloromethylene, difluoromethylene, benzylene, α-phenoxybenzylene, α,α-dimethylbenzylene, α,α-methylphenylbenzylene, diphenylmethylene and α-benzyloxybenzylene. The substituted or unsubstituted alicyclic residue includes divalent alicyclic residues having 5 to 7 carbon atoms such as cyclopentyl, cyclohexyl, 4-methylcyclohexyl and cycloheptyl.

In the compound of the general formula [5], each of $Y^1$ to $Y^8$ is independently a substituted or unsubstituted alkyl group having 1 to 20 carbon atoms or a substituted or unsubstituted aryl group having 6 to 16 carbon atoms. Specific examples of the substituted or unsubstituted alkyl group and the substituted or unsubstituted aryl group are those described concerning the above $R^1$ to $R^{48}$.

In the above compounds of the general formulae [1] to [5], the compounds of the formulae [3] to [5] which have substituents each of which has an aromatic ring, or the compounds of the general formulae [1] to [5] in which adjacent substituents indicated by $R^1$ to $R^{48}$ form aromatic rings, have increased glass transition points and melting points, and these compounds therefore show improved resistance (heat resistance) against Joule's heat generated in the organic layers, between the organic layers, or between the organic layer and the electrode of a metal. When the above compounds are used as a light-emitting material for an organic EL device, they exhibit a high light emission brightness and are advantageous in the continuous light-emitting operation over a long period of time. Examples of the above compounds of the general formulae [1] to [5] in which adjacent substituents indicated by $R^1$ to $R^{48}$ form aromatic rings are those in which $R^1$ and $R^2$ are mutually fused, $R^3$ and $R^4$ are mutually fused, $R^5$ and $R^6$ are mutually fused and $R^7$ and $R^8$ are mutually used, to form benzene rings, naphthalene rings, anthracene rings or pyrene rings. The compounds of the present invention shall not be limited to the above substituents.

The compounds of the general formulae [1] to [5] are synthesized, for example, by the following method.

9,10-Dihalogenoanthracene, an amine derivative which may have a substituted and potassium carbonate are allowed to react in a solvent in the presence of a catalyst, whereby the compounds of the general formulae [1] to [5] are synthesized. The anthracene derivative may be replaced with an anthraquinone derivative. The potassium carbonate may be replaced with sodium carbonate, potassium hydroxide, sodium hydroxide or aqueous ammonia. The catalyst is selected from a copper powder, a copper (I) chloride, tin, tin (II) chloride, pyridine, aluminum chloride or titanium tetrachloride. The solvent is selected from benzene, toluene or xylene. The method of synthesizing the compounds of the general formula [1] to [5] shall not be limited to the above method.

Specific examples of the compounds of the general formula [1] to [5] are shown in Table 1, while the compounds of the general formula [1] to [5] shall not be limited thereto.

TABLE 1

| Compound | Chemical structure |
|---|---|
| (1) | 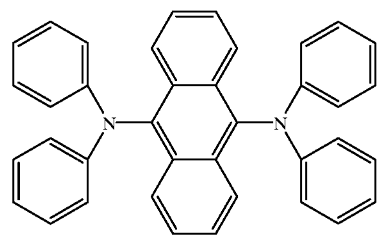 |
| (2) | 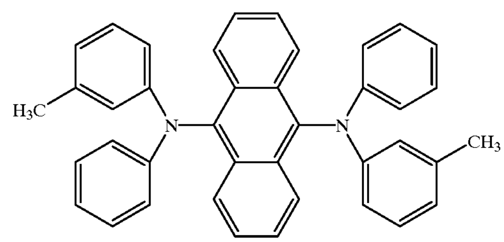 |
| (3) | 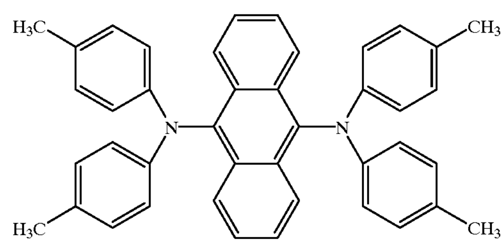 |
| (4) | 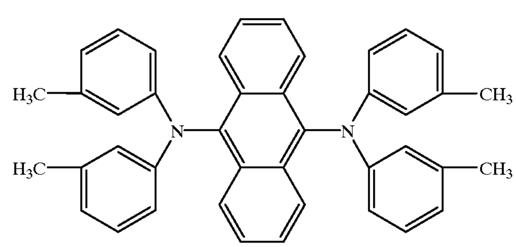 |
| (5) | 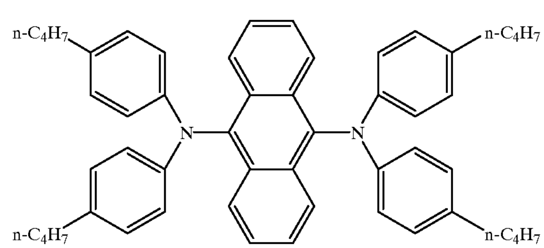 |

TABLE 1-continued

| Compound | Chemical structure |
|---|---|
| (6) | 9,10-bis[N,N-bis(4-n-octylphenyl)amino]anthracene |
| (7) | 9,10-bis[N,N-bis(4-t-octylphenyl)amino]anthracene |
| (8) | 9,10-bis[N,N-bis(4-chlorophenyl)amino]anthracene |
| (9) | 9,10-bis[N,N-bis(4-methoxyphenyl)amino]anthracene |
| (10) | 9,10-bis[N-phenyl-N-(4-methoxy-2-methylphenyl)amino]anthracene |
| (11) | 2-methyl-9,10-bis(N,N-diphenylamino)anthracene |

TABLE 1-continued

| Compound | Chemical structure |
| --- | --- |
| (12) | 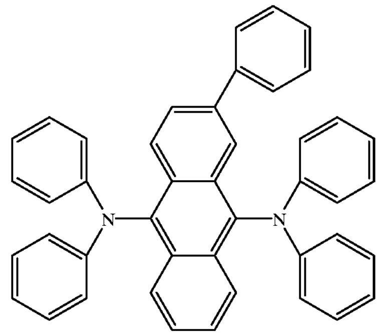 |
| (13) | 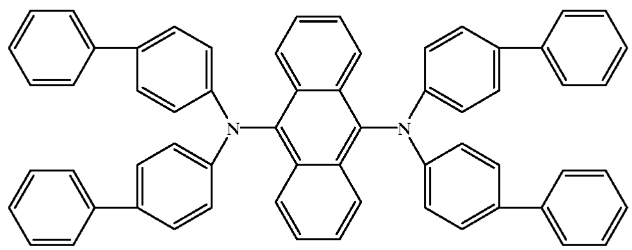 |
| (14) | 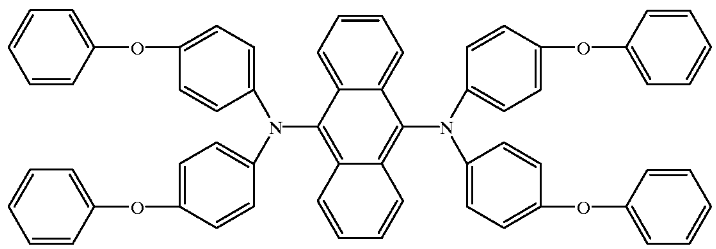 |
| (15) | 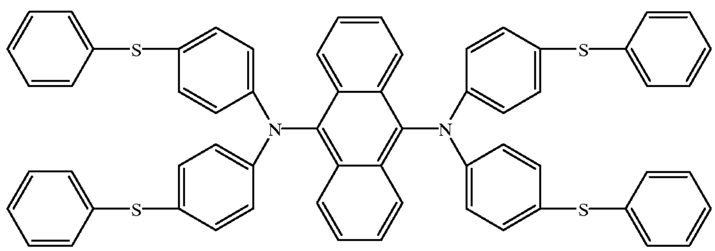 |
| (16) | 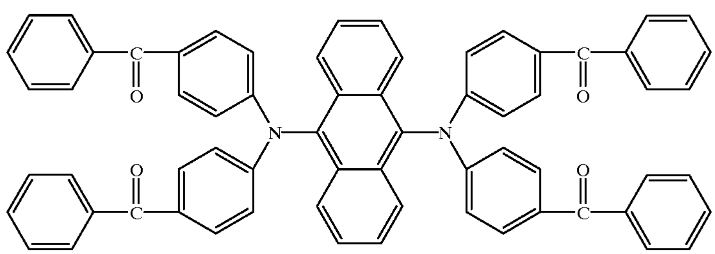 |

TABLE 1-continued

| Compound | Chemical structure |
| --- | --- |
| (17) | 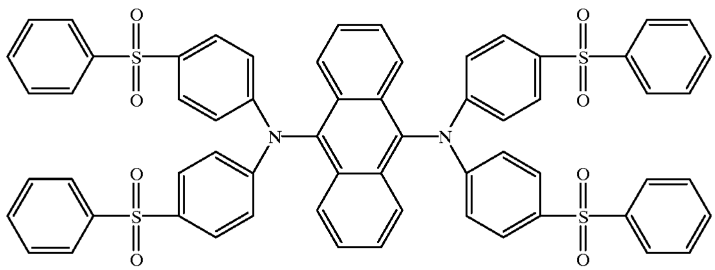 |
| (18) | 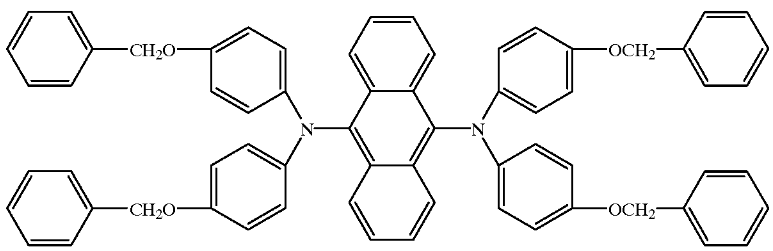 |
| (19) | 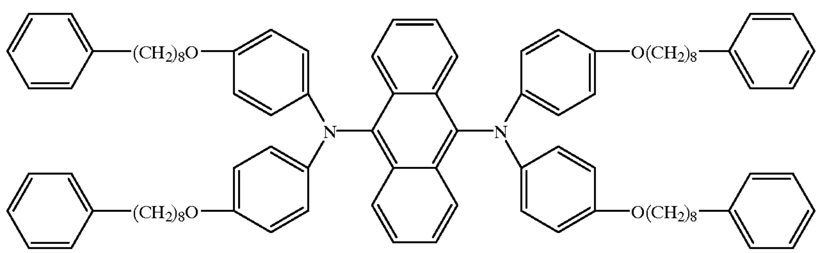 |
| (20) | 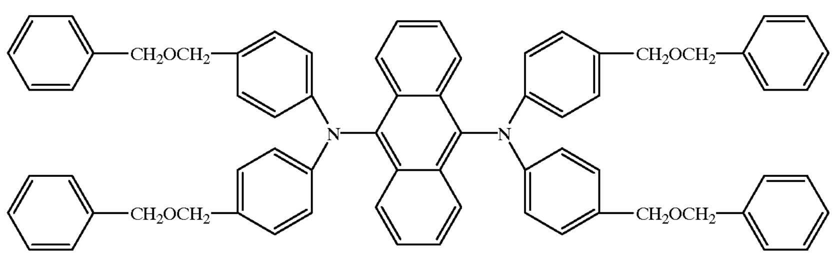 |
| (21) | 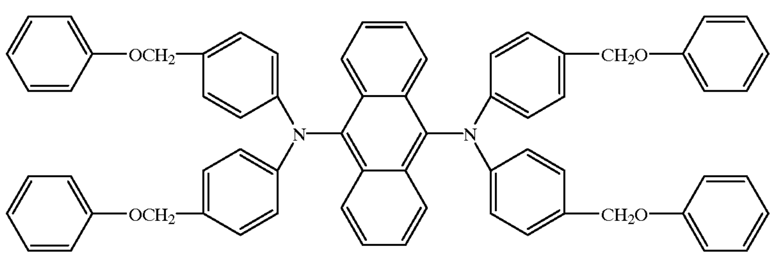 |

TABLE 1-continued

| Compound | Chemical structure |
|---|---|
| (22) | 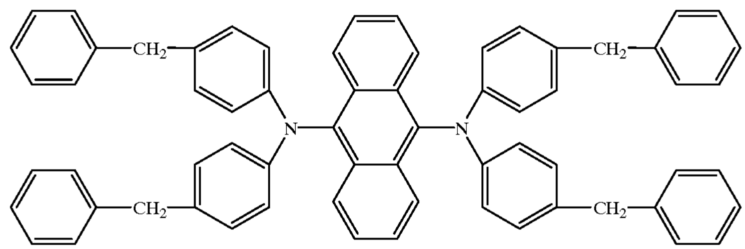 |
| (23) | 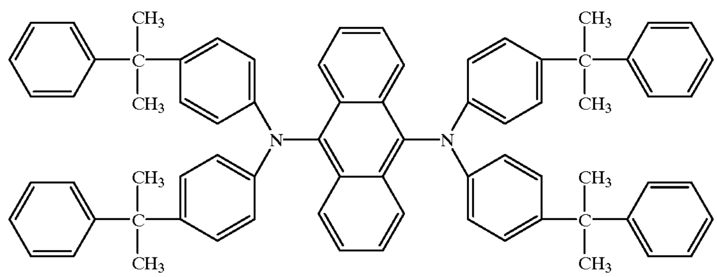 |
| (24) | 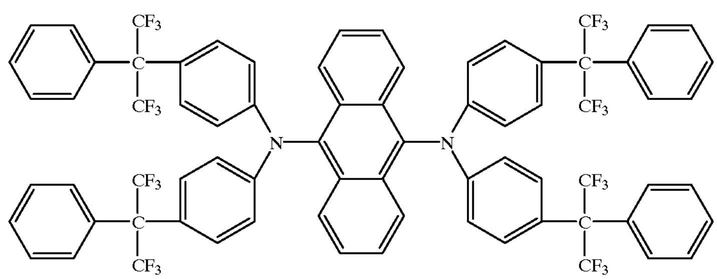 |
| (25) | 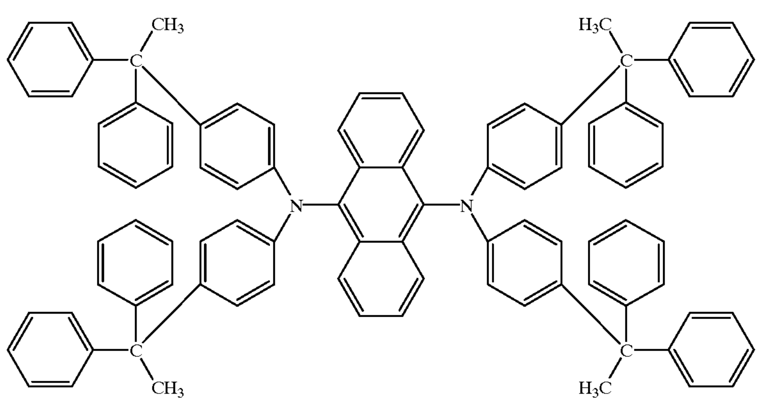 |

TABLE 1-continued
| Compound | Chemical structure |
|---|---|
| (26) | 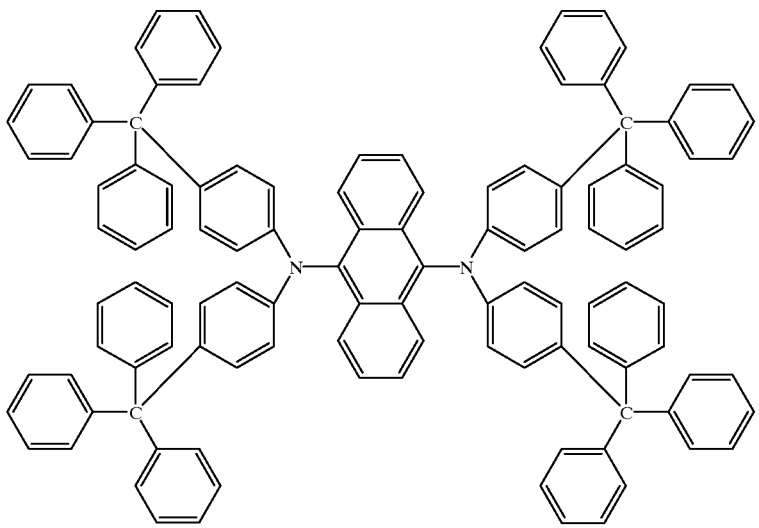 |
| (27) | 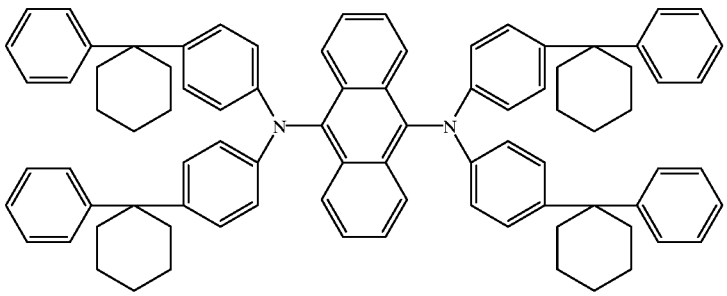 |
| (28) | 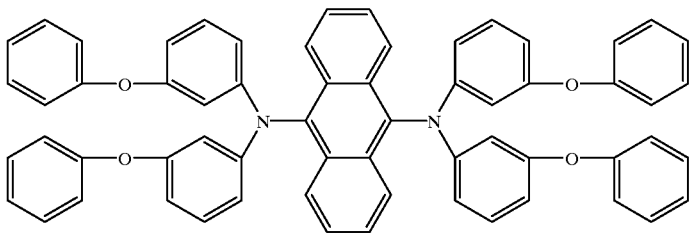 |
| (31) | 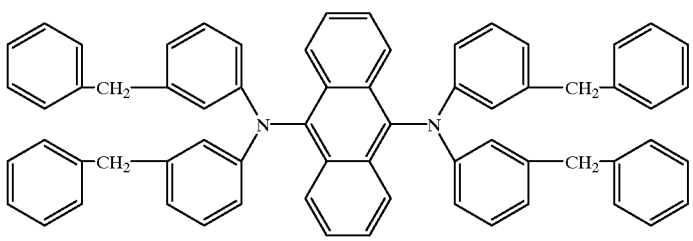 |

TABLE 1-continued

| Compound | Chemical structure |
|---|---|
| (32) | 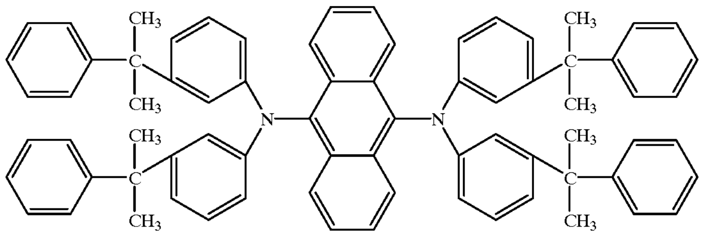 |
| (33) | 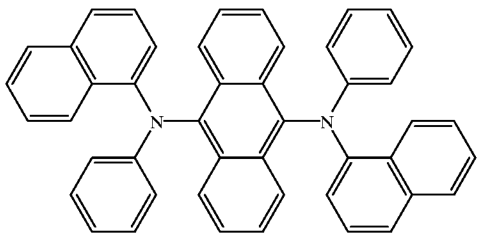 |
| (34) | 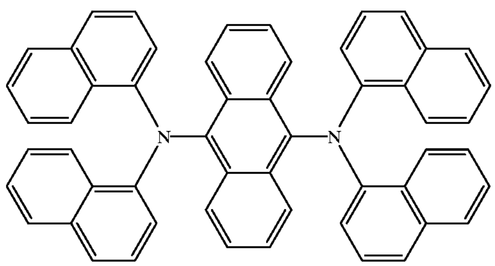 |
| (35) | 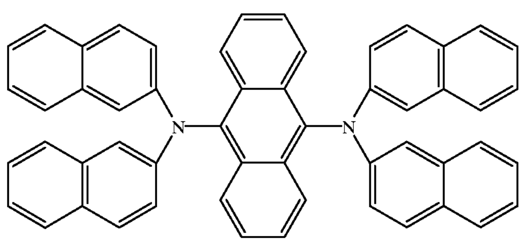 |
| (36) | 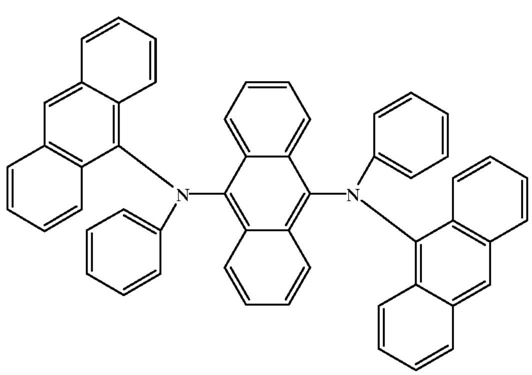 |

TABLE 1-continued

| Compound | Chemical structure |
|---|---|
| (37) | 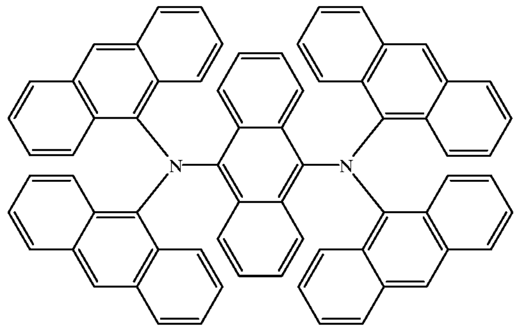 |
| (38) | 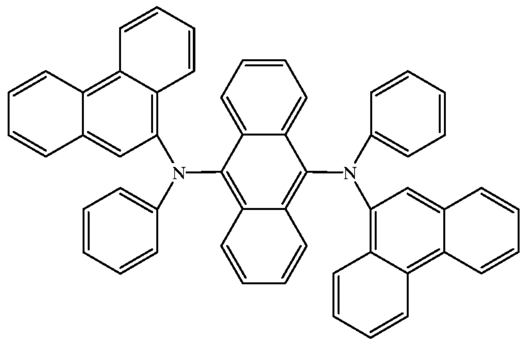 |
| (39) | 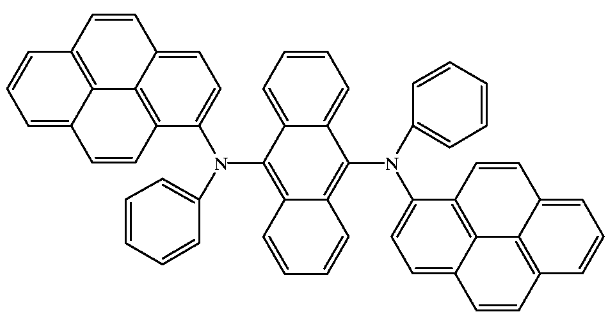 |
| (40) | 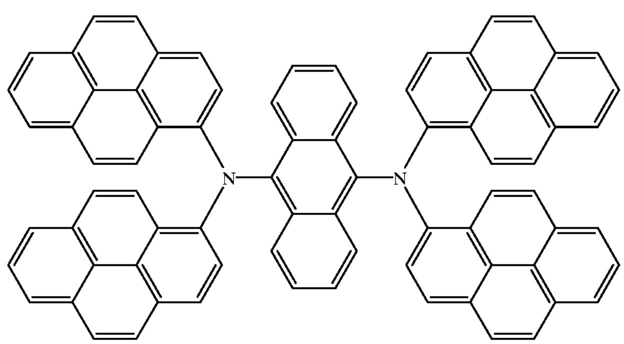 |

TABLE 1-continued

| Compound | Chemical structure |
|---|---|
| (41) | 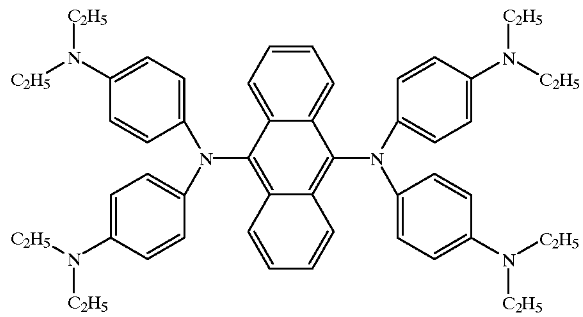 |
| (42) | 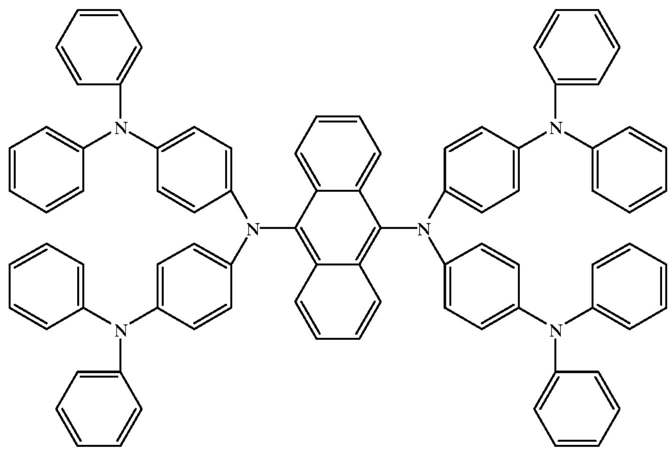 |
| (43) | 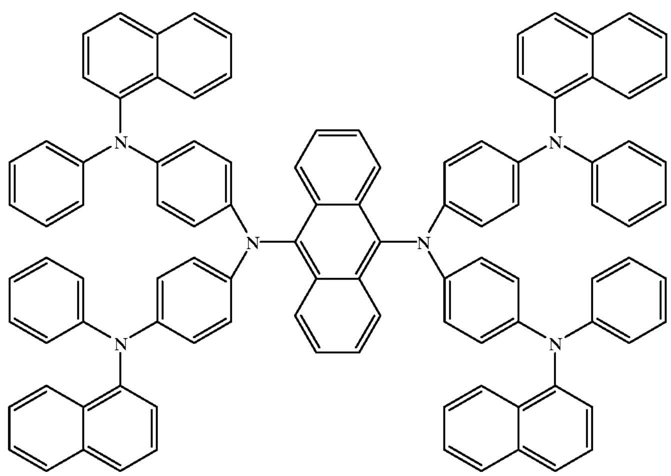 |

The compounds of the general formula [1] to [5], provided by the present invention, have intense fluorescence and are excellent in light emission when an electric field is applied. Further, the compounds of the general formula [1] to [5] can be effectively used as light-emitting materials since they have the excellent capability of being injected with, and transporting, holes from an electrode of a metal, and have the excellent capability of being injected with, and transporting, electrons from an electrode of a metal. Moreover, each of the compounds of the general formula [1] to [5] may be used in combination with other hole-transporting material, other electron-transporting material or other dopant.

The organic EL device is classified into an organic EL device of one layer type which has one organic thin layer between an anode and a cathode and an organic EL device of a multi-layer type which has a plurality of organic thin layers between an anode and a cathode. When the organic EL device is a mono-layer type, it has a light-emitting layer between an anode and a cathode. The light-emitting layer contains the light-emitting material. For transporting holes injected from the anode to the light-emitting material or transporting electrons injected from the cathode to the light-emitting material, the light-emitting layer may further contain a hole-injecting material or an electron-injecting material. However, each of the light-emitting materials of the present invention alone can be used for forming a light-emitting layer, since they all have a very high light-emitting quantum efficiency, a very high hole-injecting and hole-transporting capability and a high electron-injecting and electron-transporting capability, and are formable into a thin layer. For example, the organic EL device of a multi-layer type has a layer structure such as anode/hole-injecting layer/light-emitting layer/cathode, anode/light-emitting layer/electron-injecting layer/cathode, or anode/hole-injecting layer/light-emitting layer/electron-injecting layer/cathode. Each of the compounds of the general formula [1] to [5] can be used as a light-emitting material in the light-emitting layer since they have high light emission properties and the properties of injecting and transporting holes and injecting and transporting electrons.

The light-emitting layer may contain a known light-emitting material, a known dopant, a known hole-injecting material and a known electron-injecting material as required in combination with any one of the compounds of the general formula [1] to [5]. A multi-layer structure of the organic EL device can serve to prevent quenching from degrading the brightness and the device life. A light-emitting material, a dopant, a hole-injecting material and an electron-injecting material may be used in combination as required. Further, some dopants improve the brightness and efficiency in light emission, and serve to obtain light emission in red or blue. Further, each of the hole-injecting layer, the light-emitting layer and electron-injecting layer may have a structure of at least two layers. For example, when the hole-injecting layer has a structure of two layers, a layer into which holes are injected from an electrode will be referred to as "hole-injecting layer", and a layer which receives holes from the "hole-injecting layer" and transports the holes to the light-emitting layer will be referred to as "hole-transporting layer". Similarly, when the electron-injecting layer has a structure of two layers, a layer into which electrons are injected from an electrode will be referred to as "electron-injecting layer", and a layer which receives electrons from the "electron-injecting layer" and transports the electrons to the light-emitting layer will be referred to as "electron-transporting layer". Materials for these layers are selected depending upon factors such as their energy level, heat resistance and adhesion to other organic layer or an electrode of a metal.

The light-emitting material or the doping material used in combination with the compounds of the general formula [1] to [5] includes anthracene, naphthalene, phenanthrene, pyrene, tetracene, coronene, fluorescein, perylene, phthaloperylene, naphthaloperylene, perinone, naphthaloperinone, diphenylbutadiene, tetraphenylbutadiene, coumarine, oxadiazole, aldazine, bisbenzoxazoline, bisstyryl, pyrazine, cyclopentadiene, quinoline metal complex, aminoquinoline metal complex, benzoquinoline metal complex, imine, diphenylethylene, vinyl anthracene, diaminocarbazole, pyrane, thiopyrane, polymethine, merocyanine, an imidazole-chelated oxynoid compound, quinacridone, rubrene and fluorescence dyes, although the above materials shall not be limited to these.

The doping material has a high fluorescence intensity when it is in the state of a low concentration, and it has a decreased fluorescence intensity when it is in the state of a high concentration, particularly, in the state of a solid. Light emission is therefore effectively achieved by incorporating a low concentration of the doping material into a fluorescence material as a host, and it can be therefore expected to increase the light emission efficiency. Further, some doping materials can be used for shifting the light color from the fluorescence color of a host material to the fluorescence color of a doping material on the basis of the energy shift from the host material.

Although differing depending upon a host material used, the amount of the doping material is 0.0001 to 50% by weight, preferably 0.001 to 5% by weight.

The hole-injecting material is selected from compounds which are capable of transporting holes, receiving holes from an anode, injecting the holes into the light-emitting layer or a light-emitting material, preventing the movement of excitons generated in the light-emitting layer into the electron-injecting layer or the electron-injecting material and forming a thin film. Specifically, the above hole-injecting material includes a phthalocyanine derivative, a naphthalocyanine derivative, a porphyrin derivative, oxazole, oxadiazole, triazole, imidazole, imidazolone, imidazolthione, pyrazoline, pyrazolone, tetrahydroimidazole, hydrazone, acylhydrazone, polyarylalkane, stilbene, butadiene, benzidine type triphenylamine, styrylamine type triphenylamine, diamine type triphenylamine, derivatives of these, and polymer materials such as polyvinylcarbazole, polysilane and an electrically conductive polymer, although the above hole-injecting material shall not be limited to these.

More effective hole-injecting material that can be used for the organic EL device of the present invention are aromatic tertiary amine derivatives or phthalocyanine derivatives. Specific examples thereof include triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenathrene-9,10-dimaine, N,N-bis(4-di-4-tolylaminophenyl)-4-phenyl-cyclohexane, and oligomers or polymers having an aromatic tertiary amine skeleton thereof.

In the compound of the general formula [6] in the present invention, $B^1$ to $B^4$ is independently a substituted or unsubstituted aryl group having 6 to 16 carbon atoms. Specific examples of $B^1$ to $B^4$ include aromatic ring groups such as phenyl, biphenyl, terphenyl, naphthyl, anthryl, phenanthryl, fluorenyl and pyrenyl, and these aromatic ring groups may contain a substituent. Carbon atom(s) of the above aryl group may be replaced with at least one of N, O and S atoms. In the aryl group, a combination of $B^1$ and $B^2$ or a combination of $B^3$ and $B^4$ may form a ring including N in the general formula [6]. Examples of the aryl groups whose carbon atom is replaced with a nitrogen atom, etc., include furanyl, thiophenyl, pyrrolyl, pyranyl, thiopyranyl, pyridyl, thiazolyl, imidazolyl, pyrimidinyl, triazinyl, indolyl, quinolyl, purinyl and carbazolyl. Z is a divalent arylene group. Examples of the arylene group includes divalent aromatic ring groups such as phenylene, biphenylene, terphenylene, naphthylene, anthrylene, phenanthrylene, flourenylene and pyrenylene groups. The above arylene groups may have the same substitutents as $R^1$ to $R^{48}$ in arbitrary sites. Typical examples of the general formula [6] and other compounds which are more effective hole-injecting materials are shown in Table 2, while the present invention shall not be limited to these examples.

TABLE 2

| Compound | Chemical structure |
|---|---|
| A-1 | 2,5-bis[4-(N,N-diethylamino)phenyl]-1,3,4-oxadiazole |
| A-2 | 9-ethylcarbazole-3-carbaldehyde N,N-diphenylhydrazone |
| A-3 | 4-(diphenylamino)benzaldehyde N,N-diphenylhydrazone |
| A-4 | 4-(diphenylamino)-β,β-diphenylstyrene |
| A-5 | tri(p-tolyl)amine |
| A-6 | N,N,N′,N′-tetra(p-tolyl)-p-phenylenediamine |

TABLE 2-continued

| Compound | Chemical structure |
|---|---|
| A-7 | 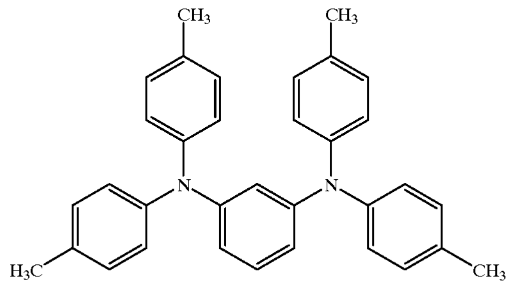 |
| A-8 | 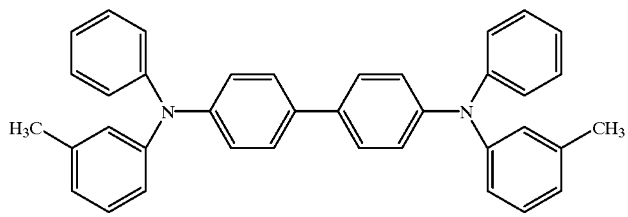 |
| A-9 | 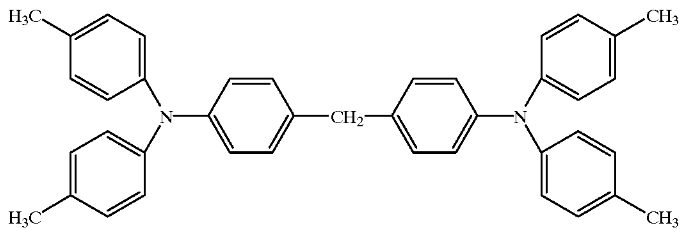 |
| A-10 | 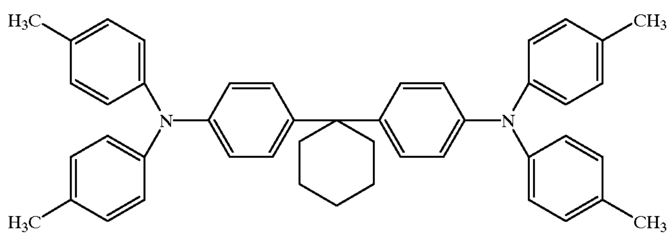 |
| A-11 | 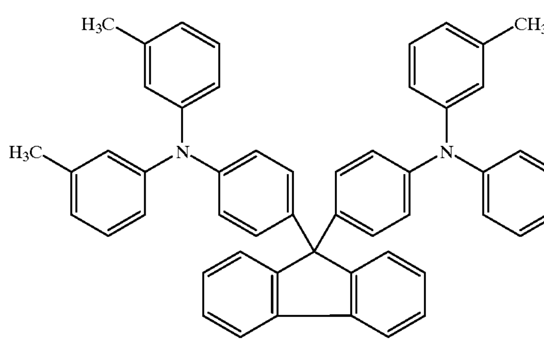 |

TABLE 2-continued

| Compound | Chemical structure |
|---|---|
| A-12 | 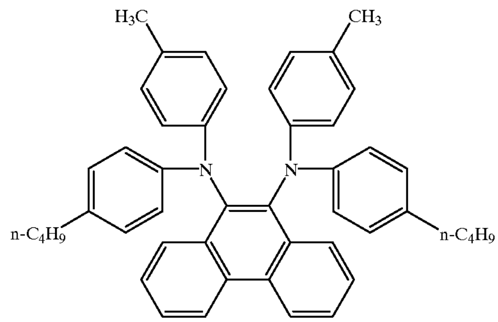 |
| A-13 | 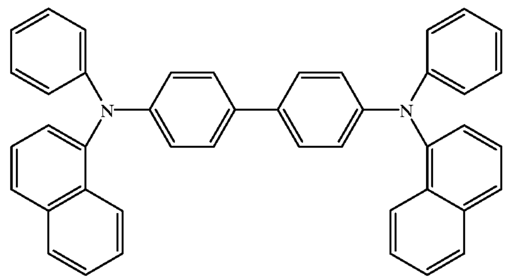 |
| A-14 | 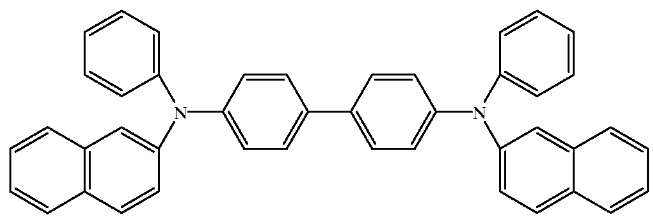 |
| A-15 | 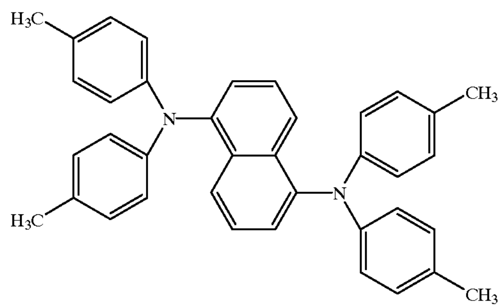 |
| A-16 | 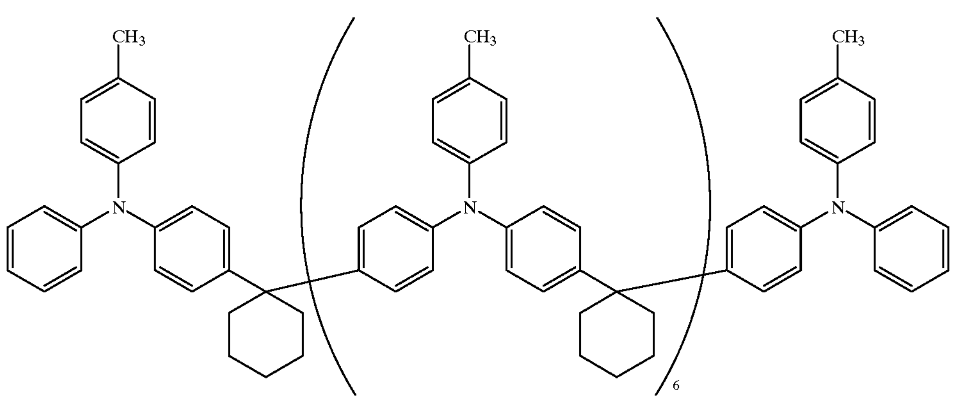 |

TABLE 2-continued

| Compound | Chemical structure |
|---|---|
| A-17 | 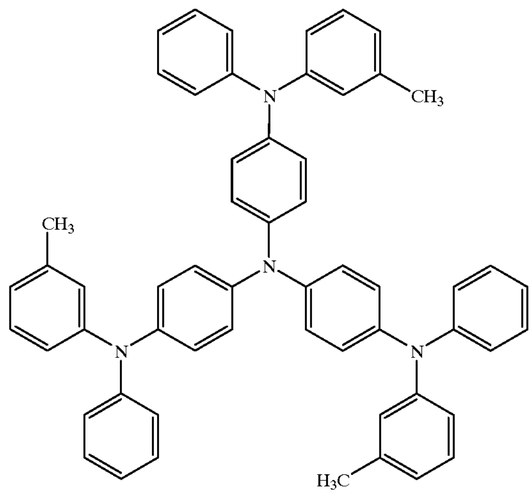 |
| A-18 | 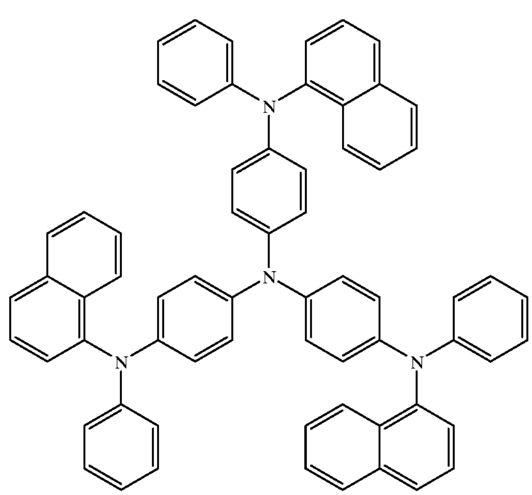 |

Examples of the phthalocyanine (Pc) derivative include H₂Pc, CuPc, CoPc, NiPc, ZnPc, PdPc, FePc, MnPc, ClAlPc, ClGaPc, ClInPc, ClSnPc, Cl₂SiPc, (HO)AlPc, (HO)CaPc, VOPc, TiOPc, MoOPc, GaPc—O—CaPc and naphthalocyanine derivatives in which the phthalocyanine skeletons of the above phthalocyanine derivatives are replaced with naphthalocyanine skeletons, while the phthalocyanine derivative shall not be limited to these.

The electron-injecting material is selected from compounds which are capable of transporting electrons, receiving electrons from a cathode, injecting the electrons into the light-emitting layer or a light-emitting material, preventing the movement of excitons generated in the light-emitting layer into the hole-injecting layer or the hole-injecting material and forming a thin film. For example, the above electron-injecting material includes fluorenone, anthraquinodimethane, diphenoquinone, thiopyran dioxide, oxazole, oxadiazole, triazole, imidazole, perylenetetracarboxylic acid, fluorenylidenemethane, anthraquinodimethane, anthrone and derivatives of these,. while the electron-injecting material shall not be limited to these. Further, the hole-transporting material may be increased in sensitivity by incorporating an electron-accepting material, and the electron-injecting material may be increased in sensitivity by incorporating an electron-donating material.

In the organic EL device of the present invention, the following metal complex compounds or nitrogen-containing five-membered derivatives are more effective electron-injecting materials. Specific examples of the metal complex compounds include lithium 8-hydroxyquinolinate, zinc bis (8-hydroxyquinolinate), copper bis (8-hydroxyquinolinate), manganese bis(8-hydroxyquinolinate), aluminum tris(8-hydroxyquinolinate), aluminum tris(2-methyl-(8-hydroxyquinolinate), gallium tris(8-hydroxyquinolinate), beryllium bis(10-hydroxybenzo[h]quinolinate), zinc bis(10-hydroxybenzo[h]quinolinate), chlorogallium bis(2-methyl-8-quinolinate), gallium bis(2-methyl-8-quinolinate)(o-cresolate), aluminum bis(2-methyl-8-quinolinate)(1-naphtholate), and gallium bis(2-methyl-8-quinolinate)(2-naphtholate), while the metal complex compounds shall not be limited to these. The nitrogen-containing five-membered derivatives are preferably oxazole, thiazole, oxadiazole, thiadiazole and triazole derivatives. Specific examples thereof include 2,5-bis(1-phenyl)-1,3,4-oxazole, dimethyl POPOP, 2,5-bis(1-phenyl)-1,3,4-thiazole, 2,5-bis(1-pheny)-

1,3,4-oxadiazole, 2-(4'-tert-butylphenyl)-5-(4"-biphenyl)1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-2,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, and 1,4-bis[2-(5-phenyltriazalyl)]benzene, while the above derivatives shall not be limited to these.

In the organic EL device of the present invention, the compound of the general formula [7] is a more effective electron-injecting material. In the general formula [7], each of $Q^1$ and $Q^2$ is independently a hydroxyquinone derivative such as 8-hydroxyquinoline, 8-hydroxyquinaldine, 8-hydroxy-2-phenylquinoline, 8-hydroxy-5-methylquinoline, 8-hydroxy-3,5,7-trifluoroquinoline. L is a halogen atom, a substituted or unsubstituted alkyl group, a substituted or unsubstituted cycloalkyl group, a substituted or unsubstituted aryl group which may contain a nitrogen atom, —OR in which R is a hydrogen atom, a substituted or unsubstituted alkyl group, a substituted or unsubstituted cycloalkyl group or a substituted or unsubstituted aryl group which may contain a nitrogen atom, or —O—Ga—$Q^3$ ($Q^4$) in which $Q^3$ and $Q^4$ have the same meanings as those of $Q^1$ and $Q^2$. The above halogen atom, alkyl group, cycloalkyl group, aryl group whose ring may contain a nitrogen atom, and the alkyl group, cycloalkyl group and aryl group whose ring may contain a nitrogen atom are those described concerning the general formulae [1] to [5].

Typical examples of the compound of the general formula [7] and typical examples of the electron-injecting material used in the present invention will be shown in the following Table 3, while the above compound and the above material shall not be limited to these.

TABLE 3

| Compound | Chemical structure |
|---|---|
| B-1 | (8-hydroxyquinoline)$_2$Zn |
| B-2 | (8-hydroxyquinoline)$_2$Mg |
| B-3 | (8-hydroxyquinoline)$_3$Al |
| B-4 | (8-hydroxyquinoline)$_3$Ga |
| B-5 | (2-methyl-8-hydroxyquinoline)$_3$Al |

TABLE 3-continued

| Compound | Chemical structure |
|---|---|
| B-6 | (2-methyl-8-quinolinolato)₃Ga |
| B-7 | bis(2-methyl-8-quinolinolato)Al–Cl |
| B-8 | bis(2-methyl-8-quinolinolato)Al–O–phenyl |
| B-9 | bis(2-methyl-8-quinolinolato)Al–O–biphenyl |
| B-10 | bis(2-methyl-8-quinolinolato)Al–O–(1-naphthyl) |
| B-11 | bis(2-methyl-8-quinolinolato)Ga–O–phenyl |

TABLE 3-continued

| Compound | Chemical structure |
| --- | --- |
| B-12 | 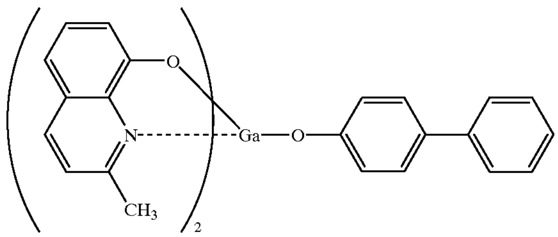 |
| B-13 | 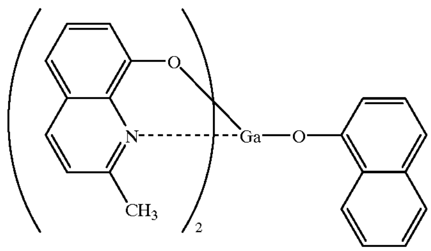 |
| B-14 | 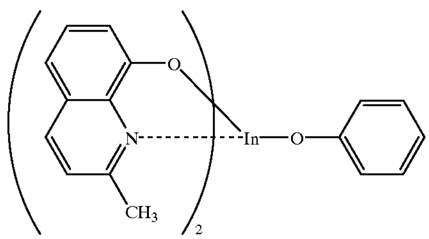 |
| B-15 | 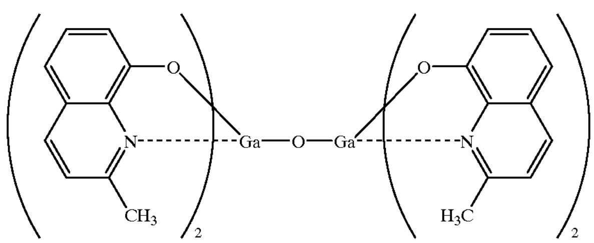 |
| B-16 | 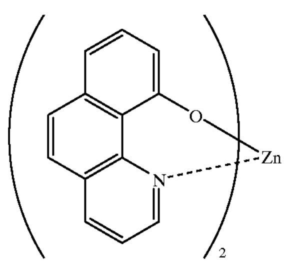 |
| B-17 | 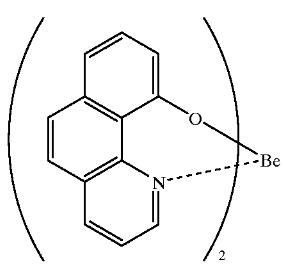 |

TABLE 3-continued

| Compound | Chemical structure |
|---|---|
| B-18 | (benzoquinoline-O,N)₂Mg |
| B-19 | (benzoquinoline-O,N)₃Al |
| B-20 | [(benzoquinoline-O,N)₂Ga]₂O |
| B-21 | 2-(4-tert-butylphenyl)-5-(4-biphenylyl)-1,3,4-oxadiazole |
| B-22 | 1,4-bis[5-(4-tert-butylphenyl)-1,3,4-oxadiazol-2-yl]benzene |
| B-23 | 2,5-bis(1-naphthyl)-1,3,4-oxadiazole |
| B-24 | 3-(4-tert-butylphenyl)-4-phenyl-5-(4-biphenylyl)-1,2,4-triazole |

In the organic EL device of the present invention, the light-emitting layer may contain at least one of other light-emitting material, dopant, hole-injecting or hole-transporting material and electron-injecting or electron-transporting material in combination with any one of the compounds of the general formulae [1] to [5]. For improving the organic EL device of its present invention in the stability against temperature, humidity and ambient atmosphere, a protective layer may be formed on the surface of the device, or the device as a whole may be sealed with a silicone oil, a resin, or the like.

The electrically conductive material used for the anode of the organic EL device is preferably selected from those materials having a work function of greater than 4 eV. This electrically conductive material includes carbon, aluminum, vanadium, iron, cobalt, nickel, tungsten, silver, gold, platinum, palladium, alloys of these, metal oxides such as tin oxide and indium oxide used for ITO substrates or NESA substrates, and organic electrically conductive resins such as polythiophene and polypyrrole.

The electrically conductive material used for the cathode is preferably selected from those having a work function of smaller than 4 eV. This electrically conductive material includes magnesium, calcium, tin, lead, titanium, yttrium, lithium, ruthenium, manganese, aluminum and alloys of these, while it shall not be limited to these. Typical examples of the alloys include magnesium/silver, magnesium/indium and lithium/aluminum, while the alloys shall not be limited to these. The metal ratio of the alloy is properly selected depending upon the temperature of a deposition source, atmosphere and the degree of vacuum. Each of the anode and the cathode may have a structure of at least two layers as required.

For the effective light emission of the organic EL device, at least one of the electrodes is desirably transparent in the light emission wavelength region of the device. Further, the substrate is desirably transparent. The transparent electrode is produced from the above electrically conductive material by a deposition method or a sputtering method such that a predetermined transparency is secured. The electrode which forms a light emission surface preferably has a light transmittance of at least 10%. The substrate is not specially limited if it has adequate mechanical and thermal strength and is transparent. For example, it is selected from transparent resin substrates such as a glass substrate, a polyethylene substrate, a polyethylene terephthalate substrate, a polyether sulfone substrate and a polypropylene substrate.

Each of the layers forming the organic EL device of the present invention can be formed by any one of dry film forming methods such as a vacuum deposition method, a sputtering method, a plasma method and an ion plating method and wet film forming methods such as a spin coating method, a dipping method and a flow coating method. The thickness of each layer is not specially limited, while each layer is required to have a proper thickness. When the layer is too thick, it is inefficient since, a high voltage is required to achieve the predetermined emission of light. When the layer is too thin, the layer is liable to have a pinhole, etc., so that sufficient light emission brightness is hard to obtain when an electric field is applied. Generally, the thickness of each layer is preferably in the range of 5 nm to 10 $\mu$m, more preferably 10 nm to 0.2 $\mu$m.

In the wet film forming method, a material for forming an intended layer is dissolved or dispersed in a proper solvent, and a thin film is formed from the solution or dispersion. The solvent is selected from chloroform, tetrahydrofuran and dioxane, while the solvent shall not be limited to these. For improving the film formability and preventing the occurrence of pinholes, the above solution or dispersion for forming the layer may contain a proper resin and a proper additive. The resin suitable for use in the present invention includes insulating resins such as polystyrene, polycarbonate, polyarylate, polyester, polyamide, polyurethane, polysulfone, polymethyl methacrylate, polymethyl acrylate and cellulose, copolymers of these, photoconductive resins such as poly-N-vinylcarbozole and polysilane, and electrically conductive resins such as polythiophene and polypyrrole. The above additive includes an antioxidant, an ultraviolet absorbent and a plasticizer.

When the light-emitting layer of the organic EL device is formed of the compound of the present invention, and when organic EL device has a specific hole-injecting layer or electron-injecting layer in combination, the organic EL device is improved in properties such as light emission efficiency, maximum light emission brightness. Further, the organic EL device is highly stable against heat and electric current, and further it gives practically usable light emission brightness at a low actuation voltage, so that the deterioration of the device, a vital problem of prior art devices, can be remarkably decreased.

The organic EL device of the present invention can be applied to a flat panel display of a wall-mountable TV set, a flat light-emitter, a light source for a copying machine or a printer, a light source for a liquid crystal display or a counter, a display board and a sign lamp. The organic EL device of the present invention has therefore greatly industrial value.

Further, the materials of the present invention can be also used in the fields of an organic EL device, an electrophotographic photoreceptor, a photoelectric converter, a solar cell and an image sensor.

EXAMPLES

The present invention will be explained with reference to Examples hereinafter, in which "%" stands for "% by weight" and "part" stands for "part by weight".

Method of Synthesis of Compound (1)

10 Parts of anthraquinone, 35 parts of diphenylamine and 15 parts of pyridine were added to 200 parts of benzene, and 40 parts of titanium tetrachloride was dropwise added at 10° C. The mixture was stirred at room temperature for 20 hours. Then, the reaction mixture was diluted with 500 parts of water, and then neutralized with a diluted sodium hydroxide aqueous solution. Then, the reaction mixture was extracted with ethyl acetate. The extract was concentrated and purified by silica gel column chromatography to give 8 parts of an acicular crystal having yellow fluorescence. The crystal was analyzed for molecular weight to show that the crystal was Compound (1). The results of elemental analysis of the product were as shown below.

Results of elemental analysis

As $C_{38}H_{28}N_2$

Calculated (%) C; 89.06, H: 5.47, N: 5.47

Found (%) C: 89.11, H: 5.55, N: 5.34

Method of Synthesis of Compound (6)

25 Parts of 9,10-dibromoanthracene, 100 parts of 4,4-di-n-octyldiphenylamine, 40 parts of potassium carbonate, 2 parts of a copper powder and 2 parts of copper (I) chloride were added to 80 parts of nitrobenzene, and the mixture was stirred under heat at 210° C. for 30 hours. Then, the reaction mixture was diluted with 500 parts of water, and then the mixture was extracted with chloroform. A chloroform layer was concentrated, purified by silica gel column chromatography and re-precipitated in n-hexane to give 28 parts of a powder having yellow fluorescence. The powder was analyzed for molecular weight to show that the powder was Compound (6). The results of elemental analysis of the product were as shown below.

Results of elemental analysis

As $C_{70}H_{92}N_2$

Calculated (%) C: 87.50, H: 9.58, N: 2.92

Found (%) C: 87.52, H: 9.53, N: 2.95

Method of Synthesis of Compound (23)

15 Parts of 9,10-diiodoanthracene, 27 parts of 4,4-diisopropyl(2-phenyl)diphenylamine, 12 parts of potassium carbonate and 0.8 parts of a copper powder were placed in a flask, and the mixture was stirred under heat at 200° C. for 30 hours. Then, the reaction mixture was diluted with 500 parts of water, and then the mixture was extracted with chloroform. A chloroform layer was concentrated, purified by silica gel column chromatography and re-precipitated in n-hexane to give 18 parts of a powder having yellow fluorescence. The powder was analyzed for molecular weight to show that the powder was Compound (23). The results of elemental analysis of the product were as shown below.

Results of elemental analysis

As $C_{74}H_{68}N_2$

Calculated (%) C: 90.24, H: 6.91, N: 2.85

Found (%) C: 90.59, H: 6.81, N: 2.60

Method of Synthesis of Compound (33)

12 Parts of 9,10-diiodoanthracene, 25 parts of 1-naphthylphenylamine, 20 parts of potassium carbonate and 0.6 parts of a copper powder were placed in a flask, and the mixture was stirred under heat at 200° C. for 30 hours. Then, the reaction mixture was diluted with 600 parts of water, and then the mixture was extracted with chloroform. A chloroform layer was concentrated, purified by silica gel column chromatography and recrystallized from n-hexane to give 27 parts of an acicular crystal having yellow fluorescence. The crystal was analyzed for molecular weight to show that the crystal was Compound (33). The results of elemental analysis of the product were as shown below.

Results of elemental analysis

As $C_{46}H_{32}N_2$

Calculated (%) C: 90.20, H: 5.23, N: 4.57

Found (%) C: 90.39, H: 5.31, N: 4.30

Example 1

Compound (3) shown in Table 1, 2,5-bis(1-naphthyl)-1,3,4-oxadiazole and a polycarbonate resin ("Panlite K-1300", supplied by Teijin Kasei) in an amount ratio of 5/3/2 were dissolved in tetrahydrofuran, and the resultant solution was spin-coated on a cleaned glass plate with an ITO electrode to form a light-emitting layer having a thickness of 100 nm. An electrode having a thickness of 150 nm was formed thereon from a magnesium/silver alloy having a magnesium/silver mixing ratio of 10/1, to obtain an organic EL device. The organic EL device showed a green light emission of about 120 (cd/m$^2$) at a direct current voltage of 5 V and a light emission efficiency of 0.70 (lm/W).

The above organic EL device was measured for light emission brightness with a LS-100 (supplied by Minolta Camera Co., Ltd.). The light emission efficiency η (lm/W) was determined on the basis of the following equation, $$\eta(lm/W) = \pi \cdot L_0(cd/m^2)/P_{in}(W/m^2)$$

in which $P_{in}$ is an applied power per unit area and $L_0$ is a brightness obtained by the measurement. In this case, a complete diffusion surface is assumed.

Organic EL devices obtained in Examples hereinafter were also measured for brightness and determined for light emission efficiency in the above manner.

Example 2

Compound (6) shown in Table 1 was vacuum-deposited on a cleaned glass plate with an ITO electrode to form a hole-injecting type light-emitting layer having a thickness of 50 nm. Then, gallium bis(2-methyl-8-quinolinate)(1-naphtholate) complex was vacuum-deposited to form an electron-injecting layer having a thickness of 10 nm. An electrode having a thickness of 100 nm was formed thereon from a magnesium/silver alloy having a magnesium/silver mixing ratio of 10/1, to obtain an organic EL device. The above hole-injecting layer and the electron-injecting layer were formed by vacuum deposition under a vacuum of $10^{-6}$ Torr at a temperature of substrate temperature. The organic EL device showed a green light emission of about 300 cd/m$^2$ at a direct current voltage of 5 V, a maximum brightness of 2,200 cd/m$^2$ and a light emission efficiency of 0.90 (lm/W).

Example 3

Compound (6) shown in Table 1 was vacuum-deposited on a cleaned glass plate with an ITO electrode to form a hole-injecting type light-emitting layer having a thickness of 50 nm. Then, gallium bis(2-methyl-8-quinolinate)(1-naphtholate) complex was vacuum-deposited to form an electron-injecting layer having a thickness of 10 nm. An electrode having a thickness of 100 nm was formed thereon from a magnesium/silver alloy having a magnesium/silver mixing ratio of 10/1, to obtain an organic EL device. The above hole-injecting layer and the electron-injecting layer were formed by vacuum deposition under a vacuum of $10^{-6}$ Torr at a temperature of substrate temperature. The organic EL device showed a green light emission of about 350 cd/m$^2$ at a direct current voltage of 5 V, a maximum brightness of 11,000 cd/m$^2$ and a light emission efficiency of 1.05 (lm/W).

Examples 4–22

Compound (A-16) shown in Table 2 was vacuum-deposited on a cleaned glass plate with an ITO electrode to form a hole-injecting layer having a thickness of 20 m. Then, a compound shown in the following Table 4 as a light-emitting material was vacuum-deposited to form a light-emitting layer having a thickness of 20 nm. Further, gallium bis(2-methyl-8-quinolinate)(1-phenolate) complex was vacuum-deposited to form an electron-injecting layer having a thickness of 20 nm. An electrode having a thickness of 150 nm was formed thereon from a magnesium/silver alloy having a magnesium/silver mixing-ratio of 10/1, to obtain an organic EL device. Each layer was formed by vacuum deposition under a vacuum of $10^{-6}$ Torr at a temperature of substrate temperature. Table 4 shows light emission characteristics of the so-obtained EL devices. The EL devices were measured for brightness at a direct current voltage of 5 V, and all of the EL devices showed a maximum brightness of at least 10,000 cd/m$^2$. As a compound of the general formula [1], those compounds of the general formula [1] in which $R^1$ to $R^2$ were aryl groups or adjacent substituents formed aromatic rings had high glass transition points and high melting points and gave EL devices excellent initial brightness and longevity when driven to emit light.

TABLE 4

| Example | Compound | Light emission brightness (cd/m²) | Light emission efficiency (lm/W) |
|---|---|---|---|
| 4 | 1 | 450 | 1.20 |
| 5 | 2 | 430 | 1.15 |
| 6 | 3 | 470 | 1.11 |
| 7 | 4 | 420 | 1.05 |
| 8 | 6 | 510 | 1.20 |
| 9 | 8 | 430 | 1.10 |
| 10 | 10 | 440 | 1.13 |
| 11 | 23 | 750 | 1.85 |
| 12 | 13 | 700 | 1.55 |
| 13 | 14 | 750 | 1.75 |
| 14 | 33 | 700 | 1.65 |
| 15 | 34 | 670 | 1.58 |
| 16 | 35 | 690 | 1.55 |
| 17 | 36 | 770 | 1.89 |
| 18 | 38 | 650 | 1.55 |
| 19 | 39 | 680 | 1.60 |
| 20 | 41 | 560 | 1.44 |
| 21 | 42 | 690 | 1.65 |
| 22 | 43 | 720 | 1.67 |

Example 23

Compound (A-16) shown in Table 2 was vacuum-deposited on a cleaned glass plate with an ITO electrode to form a hole-injecting layer having a thickness of 20 nm, and Compound (23) as a light-emitting material, shown in Table 1, was vacuum-deposited thereon to form a light-emitting layer having a thickness of 20 nm. Then, 2,5-bis(1-naphthyl)-1,3,4-oxadiazole was vacuum-deposited to form an electron-injecting layer having a thickness of 20 nm. An electrode having a thickness of 150 nm was formed thereon from a magnesium/silver alloy having a magnesium/silver mixing ratio of 10/1, to obtain an organic EL device. The organic EL device showed a green light emission of 770 cd/m² at a direct current a voltage of 5 V, a maximum brightness of 27,000 cd/m² and a light emission efficiency of 1.80 (lm/W).

Example 24

An organic EL device was obtained in the same manner as in Example 23 except that a 5 nm thick hole-injecting layer of metal-free phthalocyanine was formed between the ITO electrode and the compound (A-16). The organic EL device showed a green light emission of 1,200 cd/m² at a direct current voltage of 5 V, a maximum brightness of 29,000 cd/m² and a light emission efficiency of 1.70 (lm/W). When compared with the organic EL device obtained in Example 23, the organic EL device obtained in Example 24 showed a higher brightness on low voltage.

Example 25

An organic EL device was obtained in the same manner as in Example 23 except that the hole-injecting layer of Compound (A-16) was replaced with a 20 nm thick hole-injecting layer of metal-free phthalocyanine. The organic EL device showed a green light emission of 650 cd/m² at a direct current voltage of 5 V, a maximum brightness of 15,000 cd/m² and a light emission efficiency of 1.30 (lm/W).

Example 26

An organic EL device was obtained in the same manner as in Example 11 except that the 20 nm thick light-emitting layer of Compound (23) was replaced with a 10 nm thick light-emitting layer formed by vapor-depositing Compound (23) and Compound (C-4) shown in Table 6 in a Compound (23)/Compound (C-4) weight ratio of 100/1. The organic EL device showed a green light emission of 700 cd/m² at a direct current voltage of 5 V, a maximum brightness of 35,000 cd/m² and a light emission efficiency of 2.70 (lm/W).

Example 27

An organic EL device was obtained in the same manner as in Example 11 except that the 20 nm thick light-emitting layer of Compound (23) was replaced with a 10 nm thick light-emitting layer formed by vapor-depositing Compound (23) and the following compound in a Compound (23)/the following compound weight ratio of 100/1. The organic EL device showed an orange light emission of 500 cd/m² at a direct current voltage of 5 V, a maximum brightness of 18,000 cd/m² and a light emission efficiency of 1.65 (lm/W).

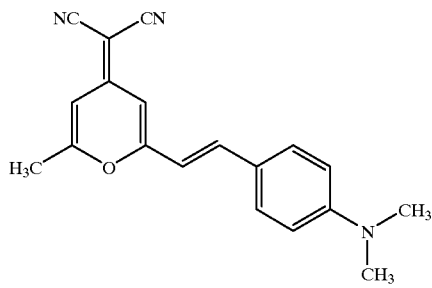

Example 28

Compound (3) shown in Table 1 as a light-emitting material, 2,5-bis(1-naphthyl)-1,3,4-oxadiazole and a polycarbonate resin ("Panlite K-1300", supplied by Teijin Kasei) in an amount ratio of 5/3/2 were dissolved in tetrahydrofuran, and the resultant solution was spin-coated on a cleaned glass plate with an ITO electrode to form a light-emitting layer having a thickness of 100 nm. An electrode having a thickness of 150 nm was formed thereon from a magnesium/silver alloy having a magnesium/silver mixing ratio of 10/1, to obtain an organic EL device. The organic EL device showed a green light emission of about 120 (cd/m²) at a direct current voltage of 5 V, a maximum brightness of 1,200 (cd/m²) and a light emission efficiency of 0.70 (lm/W).

Example 29

Compound (6) shown in Table 1 was vacuum-deposited on a cleaned glass plate with an ITO electrode to form a light-emitting layer having a thickness of 100 nm. An electrode having a thickness of 100 nm was formed thereon from a magnesium/silver alloy having a magnesium/silver mixing ratio of 10/1, to obtain an organic EL device. The above electron-injecting layer was formed by vacuum deposition under a vacuum of $10^{-6}$ Torr at a temperature of substrate temperature. The organic EL device showed a green light emission of 400 cd/m² at a direct current voltage of 5 V, a maximum brightness of 1,200 cd/m² and a light emission efficiency of 0.50 (lm/W).

Example 30

Compound (6) shown in Table 1 was vacuum-deposited on a cleaned glass plate with an ITO electrode to form a hole-injecting light-emitting layer having a thickness of 50 nm. Then, Compound (B-10) shown in Table 3 was vacuum-deposited to form an electron-injecting layer having a thickness of 10 nm. An electrode having a thickness of 100 nm was formed thereon from a magnesium/silver alloy having a magnesium/silver mixing ratio of 10/1, to obtain an organic EL device. The above hole-injecting layer and the electron-injecting layer were formed by vacuum deposition under a vacuum of $10^{-6}$ Torr at a temperature of substrate temperature. The organic EL device showed a green light emission of about 300 cd/m$^2$ at a direct current voltage of 5 V, a maximum brightness of 2,200 cd/m$^2$ and a light emission efficiency of 0.90 (lm/W).

Example 31

Compound (6) shown in Table 1 was vacuum-deposited on a cleaned glass plate with an ITO electrode to form a hole-injecting light-emitting layer having a thickness of and 50 nm. Then, Compound (B-10) shown in Table 3 was vacuum-deposited to form an electron-injecting layer having a thickness of 10 nm. An electrode having a thickness of 100 nm was formed thereon from a magnesium/silver alloy having a magnesium/silver mixing ratio of 10/1, to obtain an organic EL device. The above hole-injecting layer and the electron-injecting layer were formed by vacuum deposition under a vacuum of $10^{-6}$ Torr at a temperature of substrate temperature. The organic EL device showed a green light emission of about 350 cd/m$^2$ at a direct current voltage of 5 V, a maximum brightness of 11,000 cd/m$^2$ and a light emission efficiency of 1.05 (lm/W).

Examples 32–74

A hole-injecting material was vacuum-deposited on a cleaned glass plate with an ITO electrode under conditions shown in Table 5 to form a hole-injecting layer having a thickness of 30 m. Then, a light-emitting material was vacuum-deposited to form a light-emitting layer having a thickness of 30 nm. Further, an electron-injecting material was vacuum-deposited to form an electron-injecting layer having a thickness of 30 nm. An electrode having a thickness of 150 nm was formed thereon from a magnesium/silver alloy having a magnesium/silver mixing ratio of 10/1, to obtain an organic EL device. Each layer was formed by vacuum deposition under a vacuum of $10^{-6}$ Torr at a temperature of substrate temperature. Table 5 shows light emission characteristics of the so-obtained EL devices. The EL devices were measured for brightness at a direct current voltage of 5 V, and all of the EL devices had high-brightness characteristics, as high as a maximum brightness of at least 10,000 cd/m$^2$. The compounds of the general formula [1] to [5] gave EL devices excellent initial brightness and longevity when driven to emit light. Further, in the layer structure of the organic EL device, those EL devices which used a combination of any one of the light-emitting materials of the general formulae [1] to [5] with the hole-injecting material of the general formula [6] and the electron-injecting material of the general formula [7] showed the most excellent characteristics.

TABLE 5

| Ex. | Hole-injecting material | Light-emitting material | Electron-injecting layer | Light emission brightness (cd/m$^2$) | Maximum brightness (cd/m$^2$) | Maximum light emission efficiency (lm/W) |
|---|---|---|---|---|---|---|
| 32 | (A-2) | (1) | (B-3) | 250 | 10,200 | 0.65 |
| 33 | (A-8) | (1) | (B-3) | 430 | 16,100 | 1.5 |
| 34 | (A-10) | (1) | (B-3) | 400 | 15,000 | 1.4 |
| 35 | (A-11) | (1) | (B-3) | 430 | 15,500 | 1.6 |
| 36 | (A-12) | (1) | (B-3) | 480 | 16,000 | 1.9 |
| 37 | (A-13) | (1) | (B-3) | 520 | 18,600 | 2.1 |
| 38 | (A-16) | (1) | (B-3) | 450 | 14,000 | 1.2 |
| 39 | (A-18) | (1) | (B-3) | 410 | 15,300 | 1.5 |
| 40 | (A-13) | (1) | (B-11) | 1,100 | 23,000 | 2.8 |
| 41 | (A-13) | (6) | (B-11) | 2,300 | 56,000 | 4.7 |
| 42 | (A-13) | (10) | (B-11) | 1,300 | 33,000 | 3.1 |
| 43 | (A-13) | (11) | (B-11) | 1,000 | 22,000 | 2.5 |
| 44 | (A-13) | (13) | (B-11) | 2,200 | 32,000 | 2.5 |
| 45 | (A-13) | (14) | (B-11) | 3,000 | 58,000 | 4.3 |
| 46 | (A-13) | (18) | (B-11) | 3,500 | 78,000 | 5.1 |
| 47 | (A-13) | (22) | (B-11) | 3,500 | 69,000 | 5.0 |
| 48 | (A-13) | (23) | (B-11) | 5,100 | 110,000 | 12 |
| 49 | (A-13) | (24) | (B-11) | 5,000 | 100,000 | 10 |
| 50 | (A-13) | (25) | (B-11) | 5,600 | 125,000 | 10 |
| 51 | (A-13) | (26) | (B-11) | 4,800 | 78,000 | 8.2 |
| 52 | (A-13) | (32) | (B-11) | 3,800 | 58,000 | 7.3 |
| 53 | (A-13) | (33) | (B-11) | 3,200 | 51,000 | 5.8 |
| 54 | (A-13) | (34) | (B-11) | 3,700 | 63,000 | 5.7 |
| 55 | (A-13) | (36) | (B-11) | 3,100 | 45,000 | 4.4 |
| 56 | (A-13) | (37) | (B-11) | 3,600 | 48,000 | 5.3 |
| 57 | (A-13) | (39) | (B-11) | 2,500 | 39,000 | 3.8 |
| 58 | (A-13) | (40) | (B-11) | 2,300 | 33,000 | 3.8 |
| 59 | (A-13) | (43) | (B-11) | 2,100 | 34,000 | 3.5 |
| 60 | (A-13) | (23) | (B-1) | 2,200 | 29,000 | 3.1 |
| 61 | (A-13) | (23) | (B-4) | 1,460 | 15,000 | 1.9 |
| 62 | (A-13) | (23) | (B-5) | 1,800 | 19,000 | 2.4 |
| 63 | (A-13) | (23) | (B-6) | 1,600 | 18,500 | 2.2 |
| 64 | (A-13) | (23) | (B-10) | 2,220 | 21,000 | 3.1 |
| 65 | (A-13) | (23) | (B-12) | 4,800 | 89,000 | 8.0 |
| 66 | (A-13) | (23) | (B-13) | 4,500 | 77,000 | 7.7 |
| 67 | (A-13) | (23) | (B-15) | 3,900 | 65,300 | 7.3 |
| 68 | (A-13) | (23) | (B-16) | 3,700 | 33,000 | 4.1 |
| 69 | (A-13) | (23) | (B-21) | 2,100 | 20,000 | 3.2 |
| 70 | (A-13) | (23) | (B-22) | 2,500 | 21,000 | 3.1 |
| 71 | (A-13) | (23) | (B-23) | 2,800 | 22,000 | 2.5 |
| 72 | (A-13) | (23) | (B-24) | 2,400 | 23,000 | 2.4 |
| 73 | (A-12) | (23) | (B-11) | 5,000 | 108,000 | 11 |
| 74 | (A-8) | (14) | (B-11) | 4,500 | 71,000 | 6.9 |

Light emission brightness = brightness at a direct current voltage of 5 (V).

Example 75

A hole-injecting material (A-4) was vacuum-deposited on a cleaned glass plate with an ITO electrode to form a hole-injecting layer having a thickness of 30 nm. Then, a hole-injecting material (A-13) was vacuum-deposited to form a second hole-injecting layer having a thickness of 10 nm. Then, Compound (24) as a light-emitting material was vacuum-deposited to form a light-emitting layer having a thickness of 30 nm. Further, an electron-injecting material (B-12) was vacuum-deposited to form an electron-injecting layer having a thickness of 30 nm. An electrode having a thickness of 150 nm was formed thereon from a magnesium/silver alloy having a magnesium/silver mixing ratio of 10/1, to obtain an organic EL device. The organic EL device showed a green light emission of 1,100 cd/m$^2$ at a direct current voltage of 5 V, a maximum brightness of 87,000 cd/m$^2$ and a light emission efficiency of 9.3 (lm/W).

Example 76

A hole-injecting material (A-16) was vacuum-deposited on a cleaned glass plate with an ITO electrode to form a hole-injecting layer having a thickness of 20 nm. Then, Compound (23) as a light-emitting material was vacuum-deposited to form a light-emitting layer having a thickness of 20 nm. Further, Compound (B-23) as an electron-injecting material was vacuum-deposited to form an electron-injecting layer having a thickness of 20 nm. An electrode having a thickness of 150 nm was formed thereon from a magnesium/silver alloy having a magnesium/silver mixing ratio of 10/1, to obtain an organic EL device. The organic EL device showed a green light emission of 770 cd/m² at a direct current voltage of 5 V, a maximum brightness of 27,000 cd/m² and a light emission efficiency of 1.8 (lm/W).

Example 77

An organic EL device was obtained in the same manner as in Example 75 except that a 5 nm thick hole-injecting layer of metal-free phthalocyanine was formed between the ITO electrode and Compound (A-16). The organic EL device showed a green light emission of 1,200 cd/m² at a direct current voltage of 5 V, a maximum brightness of 29,000 cd/m² and a light emission efficiency of 1.70 (lm/W).

Example 78

An organic EL device was obtained in the same manner as in Example 75 except that the hole-injecting layer of Compound (A-16) was replaced with a 20 nm thick hole-injecting layer of metal-free phthalocyanine. The organic EL device showed a green light emission of 650 cd/m² at a direct current voltage of 5 V, a maximum brightness of 15,000 cd/m² and a light emission efficiency of 1.30 (lm/W).

Examples 79–80

An organic EL device was obtained in the same manner as in Example 75 except that the light-emitting layer was replaced with a 20 nm thick light-emitting layer formed by vapor-depositing Compound (23) and a compound shown in the following Table 6. Table 7 shows light emission characteristics of the so-obtained organic EL devices. The organic EL devices were measured for brightness at a direct current voltage of 5 V, and each organic EL device had high-brightness characteristics, as high as a maximum brightness of at least 10,000 cd/m² and emitted an intended color.

TABLE 6

| Compound | Chemical structure |
| --- | --- |
| C-1 | 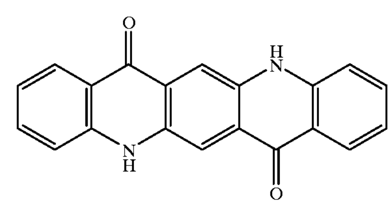 |
| C-2 | 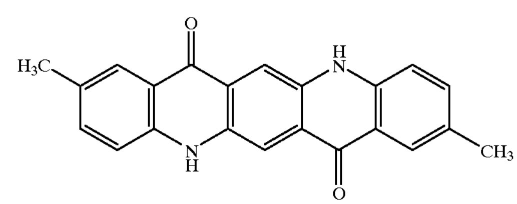 |
| C-3 | 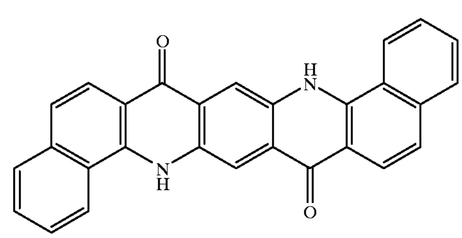 |
| C-4 | 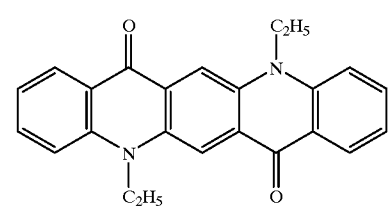 |

TABLE 6-continued

| Compound | Chemical structure |
| --- | --- |
| C-5 | 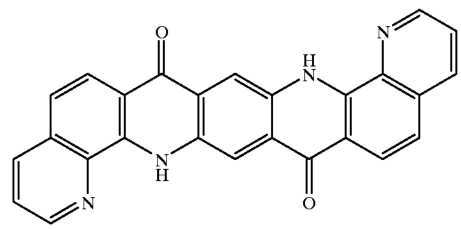 |
| C-6 | 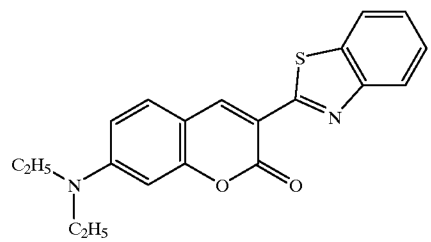 |
| C-7 | 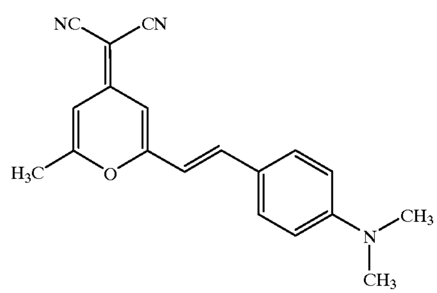 |
| C-8 | 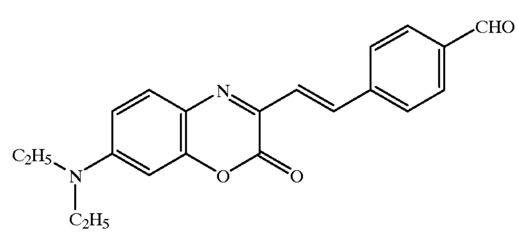 |
| C-9 | 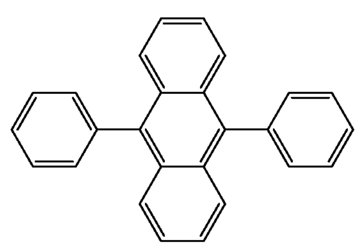 |

TABLE 6-continued

| Compound | Chemical structure |
|---|---|
| C-10 | (structure shown) |

TABLE 7

| Example | Dopant in Table 6 | Light emission brightness (cd/m²) | Maximum brightness (cd/m²) | Maximum light emission efficiency (lm/W) | Color of emitted light |
|---|---|---|---|---|---|
| 79 | (C-1) | 1,000 | 28,000 | 2.7 | Green |
| 80 | (C-2) | 850 | 25,000 | 2.7 | Green |
| 81 | (C-3) | 900 | 28,000 | 2.6 | Green |
| 82 | (C-4) | 700 | 35,000 | 2.7 | Green |
| 83 | (C-5) | 600 | 21,000 | 3.1 | Green |
| 84 | (C-6) | 500 | 22,000 | 3.0 | Green |
| 85 | (C-7) | 1,100 | 36,000 | 4.1 | Orange |
| 86 | (C-8) | 1,500 | 38,000 | 4.0 | Red |
| 87 | (C-9) | 900 | 30,000 | 3.7 | Blue |
| 88 | (C-10) | 1,100 | 31,000 | 3.5 | Yellow |

The organic EL devices obtained in the above Examples showed a light emission brightness of at least 10,000 cd/m² and high light emission efficiency. When the organic EL devices obtained in the above Examples were allowed to continuously emit light at 3 mA/cm², all the organic EL devices emitted light stably for more than 1,000 hours and showed almost no dark spots, while the light emission brightness (above 100 cd/m²) of conventional organic EL devices decreased to ½ or less than initial brightness within 500 hours. Further, the comparative organic EL devices showed many dark spots, and the number of dark spots increased, and the sizes thereof increased, with the passage of light emission time. Since the light-emitting materials of the present invention have a remarkably high fluorescence quantum effect, the organic EL devices using these light-emitting materials were able to emit light having high brightness in a range where a low voltage was applied. Further, when the dopant was used in light-emitting layers in combination with the compounds of the general formulae [1] to [5], the organic EL devices were improved in maximum light emission brightness and maximum light emission efficiency. Further, when the dopant for the red or blue light emission was added to the compounds of the general formulae [1] to [5] for the light emission of bluish green, green or yellow, the organic EL devices emitted red or blue light.

The organic EL device of the present invention is intended to achieve improvements in light emission efficiency and light emission brightness and an increase in device life, and is not to impose any limitation on other light-emitting material, dopant, hole-injecting or hole-transporting material, electron-injecting or electron-transporting material, sensitizer, resin, electrode material, and the like which are used in combination with the compounds of the present invention, nor is it to impose any limitation on the method of the production thereof.

The organic EL device for which any one of the light-emitting materials of the present invention is applied emits light having a high brightness with high light emission efficiency, and achieves a long device life, as compared with conventional devices. Therefore, the organic EL device which has at least one layer formed of any one of the light-emitting material of the present invention and has a device constitution according to the present invention shows a high brightness, high light emission efficiency and a long device life.

What is claimed is:

1. An organic electroluminescence device obtained by forming a hole-injecting layer, a light-emitting layer and an electron-injecting layer between a pair of electrodes which are an anode and a cathode, the light-emitting layer comprising at least one light-emitting material selected from the group consisting of the following general formulas:

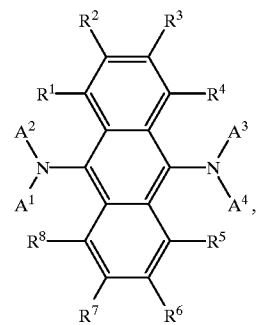

(1)

wherein each of $A^1$ to $A^4$ is a substituted or unsubstituted aryl group having 6 to 16 carbon atoms, and each of $R^1$ to $R^8$ is independently a hydrogen atom, a halogen atom, a substituted or unsubstituted alkyl group, a substituted or unsubstituted alkoxy group, a substituted or unsubstituted aryl group or a substituted or unsubstituted amino group, provided that adjacent substituents may form an aryl ring,

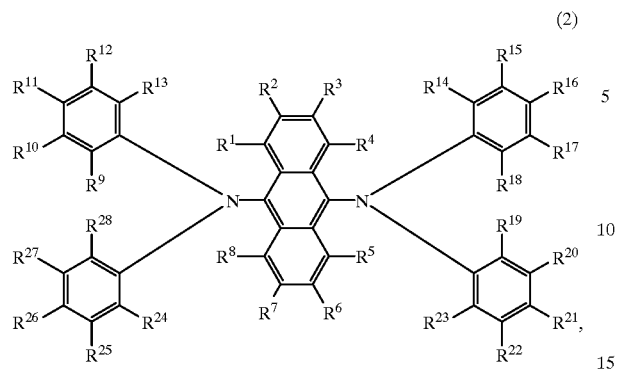

(2)

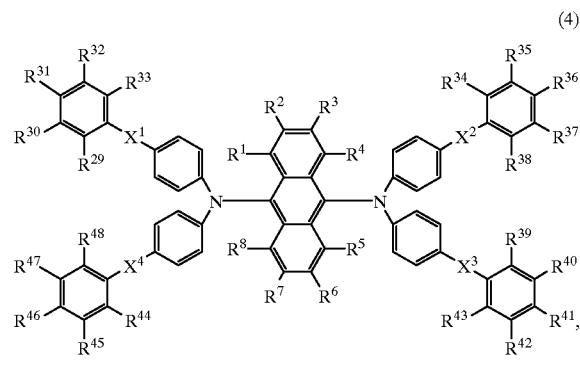

(4)

wherein each of $R^1$ to $R^{28}$ is independently a hydrogen atom, a halogen atom, a substituted or unsubstituted alkyl group, a substituted or unsubstituted alkoxy group, a substituted or unsubstituted aryl group or a substituted or unsubstituted amino group, provided that adjacent substituents of $R^1$ to $R^4$ or $R^5$ to $R^8$ may form an aryl ring, wherein each of $R^1$ to $R^8$ and $R^{29}$ to $R^{48}$ is independently a hydrogen atom, a halogen atom, a substituted or unsubstituted alkyl group, a substituted or unsubstituted alkoxy group, a substituted or unsubstituted aryl group or a substituted or unsubstituted amino group, and each of $X^1$ to $X^4$ is independently O, S, C=O, SO$_2$, $(CH_2)_x$—O—$(CH_2)_y$, a substituted or unsubstituted alkylene group or a substituted or unsubstituted alicyclic residue, provided that each of x and y is independently an integer of 0 to 20 and that x+y=0 in no case, provided that adjacent substituents of $R^1$ to $R^4$ or $R^5$ to $R^8$ may form an aryl ring, and

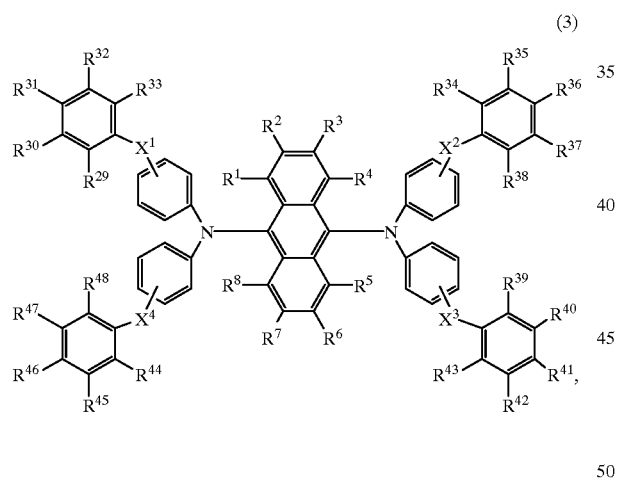

(3)

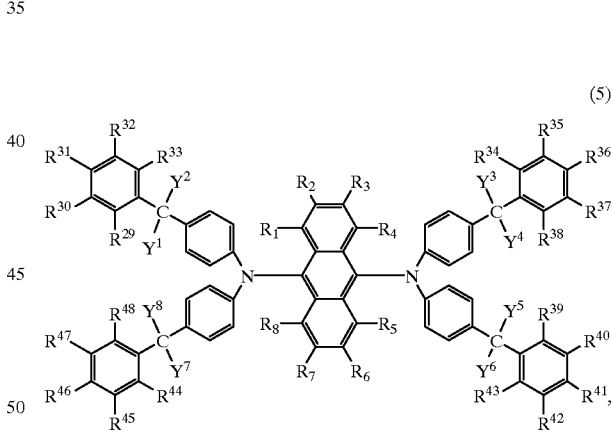

(5)

wherein each of $R^1$ to $R^8$ and $R^{29}$ to $R^{48}$ is independently a hydrogen atom, a halogen atom, a substituted or unsubstituted alkyl group, a substituted or unsubstituted alkoxy group, a substituted or unsubstituted aryl group or a substituted or unsubstituted amino group, and each of $X^1$ to $X^4$ is independently O, S, C=O, SO$_2$, $(CH_2)_x$—O—$(CH_2)_y$, a substituted or unsubstituted alkylene group or a substituted or unsubstituted alicyclic residue, provided that each of x and y is independently an integer of 0 to 20 and that x+y=0 in no case, provided that adjacent substituents of $R^1$ to $R^4$ or $R^5$ to $R^8$ may form an aryl ring, wherein each of $R^1$ to $R^8$ and $R^{29}$ to $R^{48}$ is independently a hydrogen atom, a halogen atom, a substituted or unsubstituted alkyl group, a substituted or unsubstituted alkoxy group, a substituted or unsubstituted aryl group or a substituted or unsubstituted amino group, and each of $Y^1$ to $Y^8$ is independently a substituted or unsubstituted alkyl group having 1 to 20 carbon atoms or a substituted or unsubstituted aryl group having 6 to 16 carbon atoms, provided that adjacent substituents of $R^1$ to $R^4$ or $R^5$ to $R^8$ may form an aryl ring.

2. The organic electroluminescence device according to claim 1, wherein the hole-injecting layer comprises an aromatic tertiary amine derivative.

3. The organic electroluminescence device according to claim 2, wherein the aromatic tertiary amine derivative has the following general formula (6)

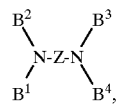

wherein each of $B^1$ to $B^4$ is independently a substituted or unsubstituted aryl group having 6 to 16 carbon atoms, and Z is a substituted or unsubstituted arylene group.

4. The organic electroluminescence device according to claim 1, wherein the hole-injecting layer comprises a phthalocyanine derivative.

5. The organic electroluminescence device according to claim 1, wherein the electron-injecting layer comprises a metal complex compound having the following general formula (7)

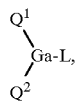

wherein each of $Q^1$ and $Q^2$ is independently a substituted or unsubstituted hydroxyquinoline derivative or a substituted or unsubstituted hydroxybenzoquinoline derivative, and L is a ligand which is a halogen atom, a substituted or unsubstituted alkyl group, a substituted or unsubstituted cycloalkyl group, a substituted or unsubstituted aryl group which may contain a nitrogen atom, —OR in which R is a hydrogen atom, a substituted or unsubstituted alkyl group, a substituted or unsubstituted cycloalkyl group or a substituted or unsubstituted aryl group which may contain a nitrogen atom, or —O—Ga—$Q^3(Q^4)$ in which $Q^3$ and $Q^4$ have the same meanings as those of $Q^1$ and $Q^2$.

6. The organic electroluminescence device according to claim 1, wherein the electron-injecting layer comprises a nitrogen-containing five-membered derivative.

7. The organic electroluminescence device according to claim 1, wherein the light-emitting layer comprises the light-emitting material of the general formula (3).

8. The organic electroluminescence device according to claim 1, wherein the light-emitting layer comprises the light-emitting material of the general formula (4).

9. The organic electroluminescence device according to claim 1, wherein the light-emitting layer comprises the light-emitting material of the general formula (5).

10. The organic electroluminescence device according to claim 1, wherein the hole-injecting layer comprises an aromatic tertiary amine derivative of the following general formula (6)

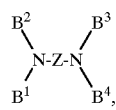

wherein each of $B^1$ to $B^4$ is independently a substituted or unsubstituted aryl group having 6 to 16 carbon atoms, and Z is a substituted or unsubstituted arylene group, and the electron-injecting layer comprises a metal complex compound of the following general formula (7)

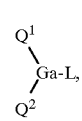

wherein each of $Q^1$ and $Q^2$ is independently a substituted or unsubstituted hydroxyquinoline derivative or a substituted or unsubstituted hydroxybenzoquinoline derivative, and L is a ligand which is halogen atom, a substituted or unsubstituted alkyl group, a substituted or unsubstituted cycloalkyl group, a substituted or unsubstituted aryl group which may contain a nitrogen atom, —OR in which R is a hydrogen atom, a substituted or unsubstituted alkyl group, a substituted or unsubstituted cycloalkyl group or a substituted or unsubstituted aryl group which may contain a nitrogen atom, or —O—Ga—$Q^3(Q^4)$ in which $Q^3$ and $Q^4$ have the same meanings as those of $Q^1$ and $Q^2$.

* * * * *